United States Patent [19]
Ullman et al.

[11] Patent Number: 6,103,537
[45] Date of Patent: Aug. 15, 2000

[54] CAPILLARY ASSAYS INVOLVING SEPARATION OF FREE AND BOUND SPECIES

[75] Inventors: Edwin F. Ullman, Atherton; Gregory B. Stauber, San Ramon, both of Calif.

[73] Assignee: ACLARA Biosciences, Inc., Mountain View, Calif.

[21] Appl. No.: 09/163,717

[22] Filed: Sep. 30, 1998

Related U.S. Application Data

[60] Provisional application No. 60/060,857, Oct. 2, 1997.

[51] Int. Cl.$^7$ .................. G01N 33/553; G01N 33/558; G01N 33/53; G01N 27/00
[52] U.S. Cl. .................. 436/526; 436/514; 436/515; 436/516; 436/517; 436/518; 436/524; 436/824; 436/527; 436/536; 436/538; 436/542; 436/540; 435/7.1; 435/7.7; 435/7.72; 435/7.79; 435/7.92; 435/7.93; 435/7.94; 435/7.95; 435/971; 422/82.01; 204/451; 204/452; 204/601; 204/603; 204/606; 204/630
[58] Field of Search .................. 436/514–518, 436/524, 526, 527, 536, 538, 542, 806, 824, 540; 435/7.1, 7.7, 7.72, 7.79, 7.92, 7.93, 7.94, 7.95, 971; 422/82.01; 204/451, 452, 601, 603, 606, 630

[56] References Cited

U.S. PATENT DOCUMENTS

| | | |
|---|---|---|
| 3,935,074 | 1/1976 | Rubenstein et al. . |
| 3,984,533 | 10/1976 | Uzgiris . |
| 3,996,345 | 12/1976 | Ulman et al. . |
| 4,098,876 | 7/1978 | Piasio et al. . |
| 4,141,687 | 2/1979 | Forrest et al. . |
| 4,275,149 | 6/1981 | Litman et al. . |
| 4,318,980 | 3/1982 | Boguslaski et al. . |
| 4,529,561 | 7/1985 | Hunt et al. . |
| 4,619,904 | 10/1986 | Giaever et al. . |
| 4,628,037 | 12/1986 | Chagnon et al. ............ 436/526 |
| 4,634,681 | 1/1987 | Giaever et al. . |
| 4,652,533 | 3/1987 | Jolley . |
| 4,695,392 | 9/1987 | Whitehead et al. ........... 252/62.54 |
| 4,772,550 | 9/1988 | Greenquist ................... 435/7 |
| 5,089,390 | 2/1992 | Davalian et al. . |
| 5,185,243 | 2/1993 | Ullman et al. . |
| 5,472,584 | 12/1995 | Rocklin et al. ............ 204/180.1 |
| 5,527,710 | 6/1996 | Nacamulli et al. . |
| 5,532,138 | 7/1996 | Singh et al. ............... 435/7.93 |
| 5,536,382 | 7/1996 | Sunzeri ..................... 204/451 |
| 5,541,113 | 7/1996 | Siddigi et al. . |
| 5,571,680 | 11/1996 | Chen ....................... 435/7.4 |
| 5,591,581 | 1/1997 | Massey et al. . |
| 5,610,017 | 3/1997 | Gudibande et al. . |
| 5,630,924 | 5/1997 | Fuchs et al. . |
| 5,685,965 | 11/1997 | Allington ................. 204/451 |
| 5,810,985 | 9/1998 | Bao et al. ................. 204/451 |
| 5,833,826 | 11/1998 | Nordman .................. 204/452 |
| 5,853,668 | 12/1998 | Begg et al. .............. 422/82.02 |
| 5,898,005 | 4/1999 | Singh et al. .............. 436/527 |

OTHER PUBLICATIONS

Broughton and Strong, *Clinical Chemistry* (1976) 22:726–732.
Butler, J., *Immunol. Meth.* (1975) 7:1–24.
Cautrecasas, J., *Biol. Chem.* (1970) 245:3059.
Chen, et al. *Clinical Chemistry* (1994) 40:1819–1822.
Frens, CT. *Nature Physical Science* (1973) 20:241.
Greenwood, et al. *Clinical Chemistry* (1977) 23(10): 1868–1872.
Hubert et al., *Proc. Nat'l. Acad. Sci.*, (1978) 75(7): 3143.
Ismail, et al, *Clinical Chemistry* (1978) 34(4): 571–579.
Johnson, et al, *J. Peptide Research* (1977) 50:365–371.
Köhler and Milstein, *Nature* (1975) 265:495–497.
MacCrindle, et al, *Clinical Chemistry* (1985), 31(9):1487–1490.
Maggio, Edward T., "Enzyme Immunoassay" (1980).
Matthews, et al. *Anal. Biochem.* (1985) 151: 205–209.
Parker, *Radioimmunoassay of Biologically Active Compounds*, Prentice Hall (1976).
Playfair, et al. *Br. Med. Bull.* (1974) 30:24–31.

*Primary Examiner*—Christopher L. Chin
*Assistant Examiner*—Pensee Do
*Attorney, Agent, or Firm*—Bertram I. Rowland; Rae-Venter Law Group, P.C.

[57] ABSTRACT

The present invention concerns methods for masking inhomogeneity of a member of a specific binding pair (sbp) employed in a capillary electroseparation. The method comprises binding the sbp member to synthetic particles that become localized during capillary electroseparation. Also disclosed is one embodiment of the present invention, which is a method for conducting a capillary electroseparation specific binding assay. The method involves the electroseparation of a labeled first member of a specific binding pair that is bound in a complex from labeled first member that is not bound in the complex. The complex comprises the first member and a second member of a specific binding pair. A combination is provided comprising a sample suspected of containing an analyte, a labeled first member of a specific binding pair, and a second member of a specific binding pair under conditions for forming a complex between labeled first member and the second member. The second member either initially or subsequent to the formation of the complex being covalently or noncovalently bound to synthetic particles that migrate uniformly during electroseparation. The combination is subjected to electroseparation and a determination is made as to whether the complex is formed. Also disclosed are kits for conducting a capillary electroseparation specific binding assay.

10 Claims, 2 Drawing Sheets

CAPILLARY ASSAYS INVOLVING SEPARATION OF FREE AND BOUND SPECIES

This application is based on and claims priority of the Provisional Application Serial No. 60/060,857, filed on Oct. 2, 1997.

BACKGROUND OF THE INVENTION

1. Field of the Invention

This invention relates to the field of specific binding assays and in particular to assays involving the separation of free and bound species. The ability to measure quantitatively or to identify a wide variety of physiologically active compounds, both naturally occurring and synthetic, has become of increasing importance, both as an adjunct to diagnosis, drug discovery and therapy. For the most part diagnostic assays of physiological fluids or biological samples for one or more analytes have required clinical laboratory determinations although there has been an increasing focus on being able to carry out assay determinations in the doctor's office and in the home. Numerous systems have been developed in efforts to try to address the various problems associated with analyses carried out in the clinical laboratory.

One problem arises with analytes whose presence in biological samples is relatively low. For these analytes greater assay sensitivity is necessary and, consequently, there is a continuing interest in providing improved and alternative methods to those which are presently generally available.

Numerous labels are used in specific binding assays including, for example, enzymes. Enzyme specific binding assays comprise qualitative and quantitative procedures in which a specific binding reaction such as, in immunological cases, an antigen-antibody reaction, is monitored by enzyme activity measurements. The term ELISA is generally used for enzyme immunoassays (EIA) that require a separation step. Reagent excess assays of specific antibodies or antigens that use an enzyme label are sometimes called immunoenzymometric assays. There are two basic types of EIA's: heterogeneous (separation required) and homogeneous (separation free) assays. In the heterogeneous systems, the activity of the enzyme label is not affected by the antigen-antibody reaction and it must be separated into fractions, one being enzyme reagent bound to antibody (or a complex) and the other being free, unbound enzyme reagent, i.e., free and bound species. The enzyme activity of either of these two fractions can be measured.

In the homogeneous systems, the enzyme activity of the assay solution is measured without a prior separation of the antibody-bound enzyme label from the free, unbound one, primarily because the activity of the bound enzyme label is significantly different from the unbound one. The various heterogeneous and homogeneous EIA's can be further characterized as either competitive or non-competitive (immunoenzymometric) assays. The characterization depends on whether the unlabeled antigen and the antigen linked to an enzyme compete for a limited number of antibody binding sites, or whether the antigen or antibody to be measured is allowed to react alone with an excess of immune reactant. For a more detailed discussion of various enzyme assay techniques, see "Enzyme Immunoassay" by Edward T. Maggio, CRC Press, Inc., Boca Raton, Fla., 1980. See also, for example, U.S. Pat. Nos. 3,690,834; 3,791,932; 3,850,578; 3,853,987; 3,867,517; 3,901,654; 3,935,074; 3,984,533; 3,996,345 and 4,098,876, which listing is not intended to be exhaustive.

Sandwich assays, particularly sandwich immunoassays, are one form of non-competitive assay that has been employed to achieve higher sensitivity in relation to competitive immunoassays. Immunoassays generally involve the use of antibodies, both monoclonal and polyclonal. However, antibodies, even monoclonal antibodies, are relatively inhomogeneous. Additionally, it is difficult to attach an exact number of labels to an antibody all at exactly the same sites. Accordingly, labeling of antibodies tends to further increase heterogeneity of antibody reagents. Other types of binding substances used in binding assays can be even more heterogeneous. For example receptors, particularly membrane bound receptors are frequently isolatable only when bound to other highly heterogeneous components.

Electrophoresis has been used for the separation and analysis of mixtures. Electrophoresis involves the migration and separation of molecules in an electric field based on differences in mobility. Various forms of electrophoresis are known including free zone electrophoresis, gel electrophoresis, isoelectric focusing and isotachophoresis. One approach to immunoassays employs capillary electrophoresis for separation of free and bound label. In capillary electrophoresis electroseparation is performed in tubes or channels of micrometer cross-sectional dimensions. Capillary electrophoresis may be used to separate an antibody-antigen complex from either the unbound form of the antigen or the antibody. Either the bound or free species may be analyzed and quantitated.

Although sandwich specific binding assays can provide much higher sensitivity than competitive assays, the heterogeneity of labeled receptors and antibodies makes the capillary electroseparation difficult to carry out. This results because the unbound and complexed form of the receptor migrates non-uniformly, thus producing broad, poorly defined, rather than sharp, well defined, distributions upon electroseparation analysis. Thus, conventional electroseparation methods may not offer significant advantages for specific binding assay applications.

Various approaches have been disclosed to overcome the inhomogeneity of large biomolecules. In one approach the electrophoretic mobility of a labeled antibody is tailored by attaching charged groups to the same labeled molecule. In another approach one antibody is labeled and the other is highly charged by means of a charge modifying moiety attached to the antibody.

2. Previous Disclosures

Compositions, methods and apparatus for ultrafast electroseparation analysis are described in U.S. Pat. No. 5,630,924 (Fuchs, et al., 1997). See also corresponding PCT application WO 96/33412.

Chen, et al., Clinical Chemistry (1994) 40:1819–1822, describe a method for simultaneous quantification of multiple drug analytes in urine, based on combining immunochemical binding with capillary electrophoretic separation and laser-induced fluorescence.

A rapid hypersensitive flowthrough immunodetection system is disclosed in PCT application WO 93/20449 (Afeyan, et al., 1993).

Greenwood, et al., (Clinical Chemistry (1977) 23(10):1868–1872) describe a radioimmunoassay for digoxin with a fully automated continuous-flow system.

U.S. Pat. No. 4,141,687 (Forrest, et al.) discloses an automatic apparatus and method for the assay of fluid samples.

MacCrindle, et al., (*Clinical Chemistry* (1985) 31(9) :1487–1490) describe a particle concentration fluorescence immunoassay technique for quantification of human immunoglobulins in serum.

A method of solid phase immunoassay incorporating a luminescent label is discussed in U.S. Pat. No. 4,652,533 (Jolley).

Ismail, et al., (*Clinical Chemistry* (1978) 34(4):571–579) describe the "Southmead System," a simple, fully automated continuous flow system for immunoassays.

SUMMARY OF THE INVENTION

One aspect of the invention concerns methods for masking inhomogeneity of a member of a specific binding pair (sbp) employed in a capillary electroseparation. The method comprises binding the sbp member to synthetic particles that migrate uniformly or become localized during capillary electroseparation.

Another embodiment of the present invention is a method for conducting a capillary electroseparation specific binding assay. The method involves the electroseparation of a labeled first member of a specific binding pair that is bound in a complex from labeled first member that is not bound in the complex. The complex comprises the first member and a second member of a specific binding pair. A combination is provided comprising a sample containing a substance suspected of being capable of binding to a second member of a specific binding pair, which substance may be an analyte, a labeled first member of a specific binding pair, and a second member of a specific binding pair under conditions for forming a complex between labeled first member and the second member. The second member, either initially or subsequent to the formation of the complex, is covalently or noncovalently bound to synthetic particles that migrate uniformly during electroseparation. The combination is subjected to electroseparation and a determination is made as to whether the complex is formed.

Another embodiment of the present invention is a method for conducting a capillary electroseparation specific binding assay. The method involves the electroseparation of a labeled first member of a specific binding pair that is bound in a complex from labeled first member that is not bound in the complex wherein the complex comprises the first member and a second member of a specific binding pair. The method comprises incubating a combination comprising a sample containing a substance suspected of being capable of binding to a second member of a specific binding pair, which substance may be an analyte, a labeled first member of a specific binding pair, and a second member of a specific binding pair under conditions for forming a complex between the labeled first member and the second member. The second member either initially or subsequent to the formation of the complex is bound to an electroactive substance that undergoes a change in charge as a result of electrochemical oxidation or reduction. The electroactive substance is subjected to electrochemical oxidation or reduction. The combination is subjected to electroseparation and a determination is made as to whether the complex is formed.

Another embodiment of the present invention is a method for conducting a capillary electroseparation specific binding assay. The method involves the electroseparation of a labeled first member of a specific binding pair that is bound in a complex from labeled first member that is not bound in the complex wherein the complex comprises the first member and a second member of a specific binding pair. A combination is provided comprising a sample containing a substance suspected of being capable of binding to a second member of a specific binding pair, which substance may be an analyte, a labeled first member of a specific binding pair, and a second member of a specific binding pair. The combination is subjected to conditions for forming a complex between the labeled first member and the second member. The second member either initially or subsequent to the formation of the complex is bound to a binder for the second member wherein the binder causes the complex to migrate uniformly during electroseparation. The combination is subjected to electroseparation and a determination is made as to whether the complex is formed.

Another aspect of the present invention is a method for conducting a capillary electroseparation specific binding assay for an analyte involving the electroseparation of a labeled first member of a specific binding pair that is bound in a complex from labeled first member that is not bound in the complex. The complex comprises the first member, the analyte and a second member of a specific binding pair. A combination comprising a sample suspected of containing an analyte, a labeled first member of a specific binding pair, and a second member of a specific binding pair is incubated under conditions for forming a complex between the analyte, the labeled first member and the second member. The second member either initially or subsequent to the formation of the complex, is bound to an electroactive substance that undergoes a change in charge as a result of electrochemical oxidation or reduction. The electroactive substance is subjected to electrochemical oxidation or reduction. The combination is subjected to electroseparation and a determination is made as to whether the complex is formed.

Another embodiment of the present invention is a method for conducting a capillary electroseparation specific binding assay. The method involves the electroseparation of a labeled first member of a specific binding pair that is bound in a complex comprising said first member, the analyte and a second member of a specific binding pair from labeled first member that is not bound in the complex. A combination is incubated. The combination comprises a sample containing a substance suspected of being capable of binding to a second member of a specific binding pair, a labeled first member of a specific binding pair, and a second member of a specific binding pair. The combination is incubated under conditions for forming a complex. The second member either initially or subsequent to the formation of the complex is covalently or noncovalently bound to synthetic particles that become localized during the electroseparation. The combination is subjected to electroseparation, which is carried out in channels formed on a surface selected from the group consisting of glass, silica and plastic. A determination is then made as to whether the complex is formed.

Another embodiment of the present invention is a kit for conducting a capillary assay. The kit comprises in packaged combination a labeled member of a specific binding pair that is capable of binding to suspendable particles in an immunoassay, suspendable particles, and a capillary assay device.

Another embodiment of the present invention is a kit for conducting a capillary assay. The kit comprises in packaged combination a labeled first member of a specific binding pair, a second member of a specific binding pair bound to, or capable of binding to, an electroactive substance, and a capillary assay device.

DETAILED DESCRIPTION OF THE INVENTION

Figure 1:
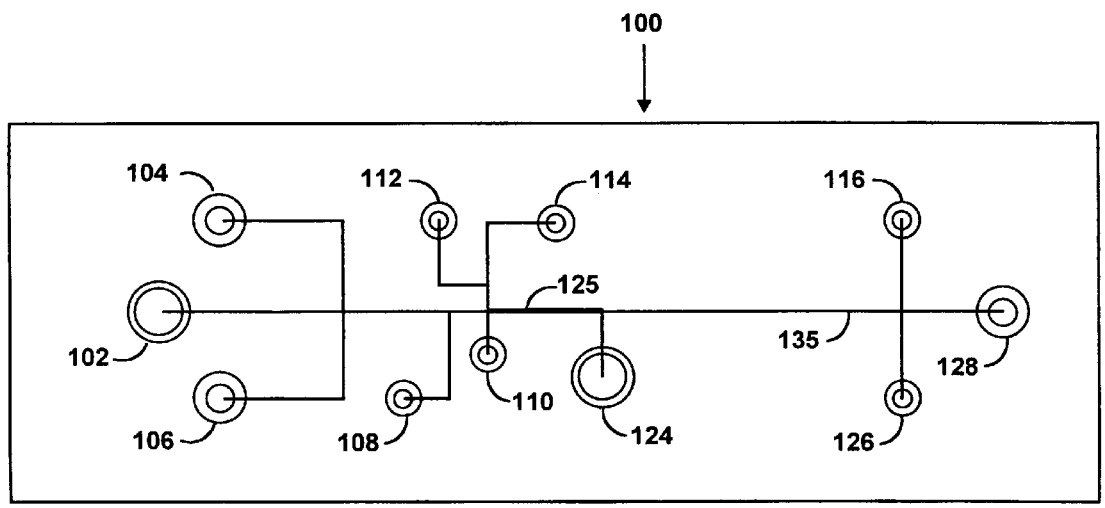
FIG. 1 is a diagram of one embodiment of a device in which reactions may be carried out in accordance with the present invention.

The present invention provides for masking inhomogeneity of a member of a specific binding pair (sbp) employed in a capillary electroseparation by employing synthetic particles that become localized during capillary electroseparation. These synthetic particles are bound to the sbp member. In conducting a capillary electroseparation specific binding assays, the synthetic particles are bound to an sbp member either initially or subsequent to the formation of a complex involving the sbp member.

The present invention is fundamentally different from known procedures. The primary application of the present invention is in the area of microfluidics involving capillary flow systems. In its broadest sense the present concept involves associating a specific binding pair member with a particle such that the associated sbp member-particle is much larger in relation to the sbp member. In this way inhomogeneity of an sbp member in capillary electroseparation procedures can be masked. This approach differs from the known approach of rendering an sbp member highly charged such as in U.S. Pat. No. 5,630,924. Accordingly, in the present invention uniform mobility of sbp members in capillary electroseparation procedures is achieved by association with a particle that migrates uniformly and becomes localized during capillary electroseparation. No charge is necessary on the particles although one may be present. It is further notable with respect to one aspect of the present invention that magnetic particles are employed in the context of electroseparation. Prior to the present invention one would not be able to predict that magnetic particles could be utilized to achieve the present results in the presence of electric fields used in electroseparation procedures. Furthermore, although magnetic particles have been used for immobilizing sbp members, this has not been done in capillary formats where considerations are much different than for macrofluidic approaches involving centrifugation, filtration, flow and the like.

Before proceeding further with a detailed description of the present invention, a number of terms as used herein are defined.

Sample—any solution, synthetic or natural, containing a substance suspected of being a member of a specific binding pair, such as an analyte, including body fluids such as, for example, whole blood, blood fractions such as serum and plasma, synovial fluid, cerebro-spinal fluid, amniotic fluid, semen, cervical mucus, sputum, saliva, gingival fluid, urine, and the like, and aqueous or water soluble solutions of natural or synthetic compounds, particularly, compounds that are potential therapeutic drugs, and it is desired to determine if the compound binds to a specific receptor. The amount of the sample depends on the nature of the sample and the analyte contained therein. For fluid samples such as whole blood, saliva, urine and the like the amount of the sample is usually about 1 to 1000 nanoliters, more usually, about 10 to 100 nanoliters. The sample can be pretreated and can be prepared in any convenient medium, which does not interfere with an electroseparation or assay in accordance with the present invention. An aqueous medium is preferred.

Substance capable of binding to a member of a specific binding pair—a compound or composition to be detected or analyzed for its specific binding properties. Such substances include, for example, analytes such as antigens, antibodies, receptors, peptides, proteins, ligands, single-stranded and double-stranded DNA, oligonucleotides, cDNA, mRNA, RNA, and the like.

Analyte—the analyte can be comprised of a member of a specific binding pair (sbp) and may be a ligand, which is monovalent (monoepitopic) or polyvalent (polyepitopic), synthetic or natural, antigenic or haptenic, and is a single compound or plurality of compounds which share at least one common epitopic or determinant site. The analyte can be a part of a cell such as bacteria or a cell bearing a blood group antigen such as A, B, D, etc., or an HLA antigen, plasma membrane receptors or a microorganism, e.g., bacterium, fungus, protozoan, or virus.

The monoepitopic ligand analytes will generally be from about 100 to 2,000 molecular weight, more usually from 125 to 1,000 molecular weight. The analytes include drugs, potential drug candidates, metabolites, pesticides, pollutants, and the like. Included among drugs of interest are the alkaloids. Among the alkaloids are morphine alkaloids, which includes morphine, codeine, heroin, dextromethorphan, their derivatives and metabolites; cocaine alkaloids, which include cocaine and benzyl ecgonine, their derivatives and metabolites; ergot alkaloids, which include the diethylamide of lysergic acid; steroid alkaloids; iminazoyl alkaloids; quinazoline alkaloids; isoquinoline alkaloids; quinoline alkaloids, which include quinine and quinidine; diterpene alkaloids, their derivatives and metabolites.

The next group of drugs includes steroids, which includes the estrogens, androgens, andreocortical steroids, bile acids, cardiotonic glycosides and aglycones, which includes digoxin and digoxigenin, saponins and sapogenins, their derivatives and metabolites. Also included are the steroid mimetic substances, such as diethylstilbestrol.

The next group of drugs is lactams having from 5 to 6 annular members, which include the barbituates, e.g., phenobarbital and secobarbital, diphenylhydantoin, primidone, ethosuximide, and their metabolites.

The next group of drugs is aminoalkylbenzenes, with alkyl of from 2 to 3 carbon atoms, which includes the amphetamines; catecholamines, which includes ephedrine, L-dopa, epinephrine; narceine; papaverine; and metabolites of the above.

The next group of drugs is benzheterocyclics, which include oxazepam, chlorpromazine, tegretol, their derivatives and metabolites, the heterocyclic rings being azepines, diazepines and phenothiazines.

The next group of drugs is purines, which includes theophylline, caffeine, their metabolites and derivatives.

The next group of drugs includes those derived from marijuana, which includes cannabinol and tetrahydrocannabinol.

The next group of drugs is the hormones such as thyroxine, cortisol, triiodothyronine, testosterone, estradiol, estrone, progestrone, polypeptides such as angiotensin, LHRH, and immunosuppresants such as cyclosporin, FK506, mycophenolic acid, and so forth.

The next group of drugs includes the vitamins such as A, B, e.g., B12, C, D, E and K, folic acid, thiamine.

The next group of drugs is prostaglandins, which differ by the degree and sites of hydroxylation and unsaturation.

The next group of drugs is the tricyclic antidepressants, which include imipramine, dismethylimipramine, amitriptyline, nortriptyline, protriptyline, trimipramine, chlomipramine, doxepine, and desmethyldoxepin, The next group of drugs is the anti-neoplastics, which include methotrexate.

The next group of drugs is antibiotics, which include penicillin, chloromycetin, actinomycetin, tetracycline, terramycin, the metabolites and derivatives.

The next group of drugs is the nucleosides and nucleotides, which include ATP, NAD, FMN, adenosine, guanosine, thymidine, and cytidine with their appropriate sugar and phosphate substituents.

The next group of drugs is miscellaneous individual drugs which include methadone, meprobamate, serotonin, meperidine, lidocaine, procainamide, acetylprocainamide, propranolol, griseofulvin, valproic acid, butyrophenones, antihistamines, chloramphenicol, anticholinergic drugs, such as atropine, their metabolites and derivatives.

Metabolites related to diseased states include spermine, galactose, phenylpyruvic acid, and porphyrin Type 1.

The next group of drugs is aminoglycosides, such as gentamicin, kanamicin, tobramycin, and amikacin.

Among pesticides of interest are polyhalogenated biphenyls, phosphate esters, thiophosphates, carbamates, polyhalogenated sulfenamides, their metabolites and derivatives.

The polyvalent ligand analytes will normally be poly (amino acids), i.e., polypeptides and proteins, polysaccharides, nucleic acids, and combinations thereof. Such combinations include components of bacteria, viruses, chromosomes, genes, mitochondria, nuclei, cell membranes and the like.

For the most part, the polyepitopic ligand analytes to which the subject invention can be applied will have a molecular weight of at least about 5,000, more usually at least about 10,000. In the poly(amino acid) category, the poly(amino acids) of interest will generally be from about 5,000 to 5,000,000 molecular weight, more usually from about 20,000 to 1,000,000 molecular weight; among the hormones of interest, the molecular weights will usually range from about 5,000 to 60,000 molecular weight.

A wide variety of proteins may be considered as to the family of proteins having similar structural features, proteins having particular biological functions, proteins related to specific microorganisms, particularly disease causing microorganisms, etc. Such proteins include, for example, immunoglobulins, cytokines, enzymes, hormones, cancer antigens, nutritional markers, tissue specific antigens, etc. Such proteins include, by way of illustration and not limitation, protamines, histones, albumins, globulins, scleroproteins, phosphoproteins, mucoproteins, chromoproteins, lipoproteins, nucleoproteins, glycoproteins, T-cell receptors, proteoglycans, HLA, unclassified proteins, e.g., somatotropin, prolactin, insulin, pepsin, proteins found in human plasma, blood clotting factors, protein hormones such as, e.g., follicle-stimulating hormone, luteinizing hormone, luteotropin, prolactin, chorionic gonadotropin, tissue hormones, cytokines, cancer antigens such as, e.g., PSA, CEA, a-fetoprotein, acid phosphatase, CA19.9 and CA125, tissue specific antigens, such as, e.g., alkaline phosphatase, myoglobin, CPK-MB and calcitonin, and peptide hormones. Other polymeric materials of interest are mucopolysaccharides and polysaccharides.

For receptor analytes, the molecular weights will generally range from 10,000 to $2 \times 10^8$, more usually from 10,000 to $10^6$. For immunoglobulins, IgA, IgG, IgE and IgM, the molecular weights will generally vary from about 160,000 to about $10^6$. Enzymes will normally range from about 10,000 to 1,000,000 in molecular weight. Natural receptors vary widely, generally being at least about 25,000 molecular weight and may be $10^6$ or higher molecular weight, including such materials as avidin, DNA, RNA, thyroxine binding globulin, thyroxine binding prealbumin, transcortin, etc.

The term analyte further includes polynucleotide analytes such as those polynucleotides defined below. These include m-RNA, r-RNA, t-RNA, DNA, DNA-RNA duplexes, etc. The term analyte also includes receptors that are polynucleotide binding agents, such as, for example, restriction enzymes, activators, repressors, nucleases, polymerases, histones, repair enzymes, chemotherapeutic agents, and the like.

The analyte may be a molecule found directly in a sample such as biological tissue, including body fluids, from a host. The sample can be examined directly or may be pretreated to render the analyte more readily detectable. Furthermore, the analyte of interest may be determined by detecting an agent probative of the analyte of interest such as a specific binding pair member complementary to the analyte of interest, whose presence will be detected only when the analyte of interest is present in a sample. Thus, the agent probative of the analyte becomes the analyte that is detected in an assay.

Specific binding—the specific recognition of one of two different molecules for the other compared to substantially less recognition of other molecules. Members of a specific binding pair have a particular affinity or avidity for each other. Generally, the molecules have areas on their surfaces or in cavities giving rise to specific recognition between the two molecules. Exemplary of specific binding are antibody-antigen interactions, enzyme—substrate interactions, polynucleotide interactions, and so forth.

Non-specific binding—non-covalent binding between molecules that is relatively independent of specific surface structures. Non-specific binding may result from several factors including hydrophobic interactions between molecules.

Member of a specific binding pair ("sbp" member)—one of two different molecules having an area on the surface or in a cavity that specifically binds to and is therefore defined as complementary with a particular spatial and polar organization of the other molecule. The members of the sbp can be referred to as ligand and receptor such as members of an immunological pair, e.g., antigen-antibody, cell surface receptor and an effector agent, and so forth. Complementary sbp members bind to one another, as for example, a ligand and its complementary receptor. With respect to two complementary sbp members, one may be referred to as the "binding partner" for the other. Sbp members can be immunological pairs such as antigen and antibody, or non-immunological pairs such as avidin and biotin. Sbp members can also be small molecules or residues of small molecules and their receptors. Small molecules have a molecular weight of from 100–2000, preferably 150–1000, and a receptor for the small molecule either exists or can be prepared. Examples of small molecules include derivatives of biotin, lysergic acid, fluorescein or a fluorescein derivative, and vitamin B12, with the corresponding receptors being avidin or streptavidin, anti-lysergic acid, anti-fluorescein and intrinsic factor, respectively.

Ligand—any organic compound for which a receptor naturally exists or can be prepared.

Ligand analog—a modified ligand, an organic radical or analyte analog, usually of a molecular weight greater than 100, which can compete with the analogous ligand for a receptor, the modification providing means to join a ligand analog to another molecule. The ligand analog will usually differ from the ligand by more than replacement of a hydrogen with a bond, which links the ligand analog to a hub or label, but need not. The ligand analog can bind to the receptor in a manner similar to the ligand. The analog could be, for example, an antibody directed against the idiotype of an antibody to the ligand.

Receptor ("antiligand")—any compound or composition capable of recognizing a particular spatial and polar organization of a molecule, e.g., epitopic or determinant site. Illustrative receptors include membrane bound receptors such as G protein coupled receptors (e.g., adrenergics, bradykinin, chemokines, cholecystokinin, dopaminergics, endothelin, muscarinics, nociceptin, opioid, prostaglandin, and serotonin), ligand-gated ion channels (e.g., excitatory amino acids and neuronal nAChR), growth factor receptors (e.g., insulin-like IGF, epidermal EGF, nerve NGF, fibroblast FGF growth factors), and the cytokines (e.g., interleukins 1–6 and interferons), D2 receptor, dopamine receptor and other naturally occurring receptors, e.g., thyroxine binding globulin, antibodies, enzymes, Fab fragments, lectins, nucleic acids, protein A, complement component C1q, and the like.

Label or reporter molecule—a chemical entity capable of being detected by a suitable detection means, including, but not limited to, spectrophotometric, chemiluminescent, electrochemical or radiochemical means. The reporter molecule can be conjugated to another molecule such as an sbp member, e.g., a ligand or an antibody, by procedures well known in the art. Typically, the reporter molecule contains a functional group suitable for attachment to the sbp member. The functional groups suitable for attaching the reporter group are usually activated esters or alkylating agents. Details of techniques for attaching reporter groups are well known in the art. See, for example, Matthews, et al., *Anal. Biochem.* (1985) 151:205–209 and Engelhardt, et al., European Patent Application No. 0302175.

Reporter molecules are members of a signal producing system capable of being detected directly or through a specific binding reaction to produce a detectable signal. The reporter molecule can be isotopic or nonisotopic, usually nonisotopic, and can be a catalyst, dye, fluorescent molecule, chemiluminescent molecule, coenzyme, enzyme, substrate, radioactive group, certain particles such as carbon and the like.

Antibody—an immunoglobulin that specifically binds to, and is thereby defined as complementary with, a particular spatial and polar organization of another molecule. The antibody can be monoclonal or polyclonal and can be prepared by techniques that are well known in the art such as immunization of a host and collection of sera (polyclonal) or by preparing continuous hybrid cell lines and collecting the secreted protein (monoclonal), or by cloning and expressing nucleotide sequences or mutagenized versions thereof coding at least for the amino acid sequences required for specific binding of natural antibodies. Antibodies may include a complete immunoglobulin or fragment thereof, which immunoglobulins include the various classes and isotypes, such as IgA, IgD, IgE, IgG1, IgG2a, IgG2b and IgG3, IgM, etc. Fragments thereof may include Fab, Fv and F(ab')2, Fab', and the like. In addition, aggregates, polymers, and conjugates of immunoglobulins or their fragments can be used where appropriate so long as binding affinity for a particular molecule is maintained.

Antiserum containing antibodies (polyclonal) is obtained by well-established techniques involving immunization of an animal, such as a rabbit, guinea pig, or goat, with an appropriate immunogen and obtaining antisera from the blood of the immunized animal after an appropriate waiting period. State-of-the-art reviews are provided by Parker, Radioimmunoassay of Biologically Active Compounds, Prentice-Hall (Englewood Cliffs, N.J., U.S., 1976), Butler, *J. Immunol. Meth.* (1975) 7: 1–24; Broughton and Strong, *Clin. Chem.* (1976) 22:726–732; and Playfair, et al., *Br. Med. Bull.* (1974) 30: 24–31.

Antibodies can also be obtained by somatic cell hybridization techniques, such antibodies being commonly referred to as monoclonal antibodies. Monoclonal antibodies may be produced according to the standard techniques of Kbhler and Milstein, *Nature* 265:495–497, 1975. Reviews of monoclonal antibody techniques are found in Lymphocyte Hybridomas, ed. Melchers, et al. Springer-Verlag (New York 1978), *Nature* 266: 495 (1977), *Science* 208: 692 (1980), and *Methods of Enzymology* 73 (Part B): 3–46 (1981). Samples of an appropriate immunogen preparation are injected into an animal such as a mouse and, after a sufficient time, the animal is sacrificed and spleen cells obtained. Alternatively, the spleen cells of a non-immunized animal can be sensitized to the immunogen in vitro. The spleen cell chromosomes encoding the base sequences for the desired immunoglobins can be compressed by fusing the spleen cells, generally in the presence of a non-ionic detergent, for example, polyethylene glycol, with a myeloma cell line. The resulting cells, which include fused hybridomas, are allowed to grow in a selective medium, such as HAT-medium, and the surviving immortalized cells are grown in such medium using limiting dilution conditions. The cells are grown in a suitable container, e.g., microtiter wells, and the supernatant is screened for monoclonal antibodies having the desired specificity.

Various techniques exist for enhancing yields of monoclonal antibodies, such as injection of the hybridoma cells into the peritoneal cavity of a mammalian host, which accepts the cells, and harvesting the ascites fluid. Where an insufficient amount of the monoclonal antibody collects in the ascites fluid, the antibody is harvested from the blood of the host. Alternatively, the cell producing the desired antibody can be grown in a hollow fiber cell culture device or a spinner flask device, both of which are well known in the art. Various conventional ways exist for isolation and purification of the monoclonal antibodies from other proteins and other contaminants (see Kbhler and Milstein, supra).

In another approach for the preparation of antibodies the sequence coding for antibody binding sites can be excised from the chromosome DNA and inserted into a cloning vector which can be expressed in bacteria to produce recombinant proteins having the corresponding antibody binding sites.

In general, antibodies can be purified by known techniques such as chromatography, e.g., DEAE chromatography, ABx chromatography, and the like, filtration, and so forth.

Hapten—a compound capable of binding specifically to corresponding antibodies, but not capable itself to act as an immunogen (or antigen) for preparation of antibodies. Antibodies that recognize a hapten can be prepared against compounds comprised of the hapten linked to an immunogenic (or antigenic) carrier. Haptens are a subset of ligands.

Immunogenic carrier—a group which, when conjugated to a hapten and injected into a mammal, will induce an immune response and elicit the production of antibodies that bind to the hapten, in this case MPA. Immunogenic carriers are also referred to as antigenic carriers. Typical immunogenic carriers include, without limitation, poly(amino acids), polysaccharides, nucleic acids and particles (biologic and synthetic materials). A wide variety of such carriers are disclosed in Davalian, et al., U.S. Pat. No. 5,089,390, column 4, line 57 to column 5, line 5, incorporated herein by reference. Other suitable immunogenic carriers include albumins, serum proteins, e.g., globulins, ocular lens proteins and lipoproteins. Illustrative proteins include bovine serum albumin, keyhole limpet hemocyanin ("KLH"), egg ovalbumin and bovine gamma globulin.

Signal producing system ("sps")—one or more components, at least one component being a detectable label or reporter molecule, which generate a detectable signal that relates to the amount of bound and/or unbound label, i.e., the amount of label bound or not bound to the compound being detected. ⊞ label and optionally other sps members are bound to an sbp member. Preferably, the label is an enzyme such as alkaline phosphatase and so forth, a chemiluminescent compound such as luminol, acridinium compound, electroluminescent group such as a transition metal complex (see, e.g., U.S. Pat. Nos. 5,541,113, 5,610,017, 5,527,710, 5,591,581, the relevant disclosures of which are incorporated herein by reference), electroactive tags, or fluorescer. Thus, with the above labels the signal is preferably detected and/or measured by detecting enzyme activity, luminescence, or light emissions, respectively. The labels and other reagents of the signal producing system must be stable at the temperatures used in the electroseparation method and subsequent assay.

Suitable labels include, by way of illustration and not limitation, enzymes such as alkaline phosphatase, glucose-6-phosphate dehydrogenase ("G6PDH") and horseradish peroxidase; promoters; dyes; fluorescers, such as fluorescein, isothiocyanate, rhodamine compounds, phycoerythrin, phycocyanin, allophycocyanin, o-phthaldehyde, and fluorescamine; electroluminescent labels such as ruthenium chelates; chemiluminescers such as isoluminol; sensitizers; coenzymes; enzyme substrates; radiolabels such as 125I, 131I, 14C, 3H, 57Co and 75Se. Suitable enzymes and coenzymes are disclosed in Litman, et al., U.S. Pat. No. 4,275,149, columns 19–28, and Boguslaski, et al., U.S. Pat. No. 4,318,980, columns 10–14; suitable fluorescers and chemiluminescers are disclosed in Litman, et al., U.S. Pat. No. 4,275,149, at columns 30 and 31; which are incorporated herein by reference.

Some labels can directly produce a signal, and therefore, additional components are not required to produce a signal. Numerous organic molecules, for example fluorescers, are able to absorb ultraviolet and visible light, where the light absorption excites these molecules to an excited energy state. This absorbed energy is then dissipated by emission of light at a second wavelength. Other labels that directly produce a signal include radioactive isotopes and dyes.

Alternately, the label may need other components to produce a signal. In this situation the signal producing system would then include all the components required to produce a measurable signal. These components may include substrates, electron transfer agents, coenzymes, enhancers, additional enzymes, substances that react with enzymatic products, catalysts, activators, cofactors, inhibitors, scavengers, metal ions, and a specific binding substance required for binding of signal generating substances. A detailed discussion of suitable signal producing systems can be found in Ullman, et al. U.S. Pat. No. 5,185,243, columns 11–13, incorporated herein by reference.

The label can be bound covalently to numerous sbp members: an antibody; a receptor for an antibody; a receptor that is capable of binding to a small molecule conjugated to an antibody, a ligand analog, an oligonucleotide and the like. Bonding of the label to the sbp member may be accomplished by chemical reactions that result in replacing a hydrogen atom of the label with a bond to the sbp member or may include a linking group between the label and the sbp member. Other sps members may also be bound covalently to sbp members. For example, two sps members such as a fluorescer and quencher can each be bound to a different antibody that forms a specific complex with the analyte. Formation of the complex brings the fluorescer and quencher in close proximity, thus permitting the quencher to interact with the fluorescer to produce a signal. Methods of conjugation are well known in the art. See for example, Rubenstein, et al., and U.S. Pat. No. 3,817,837, incorporated herein by reference. Alternatively, one label may be bound to the particles of this invention and a second label bound to a sbp member that binds to the sbp member attached to the particle.

Ancillary Materials—Various ancillary materials will frequently be employed in an assay in accordance with the present invention. For example, buffers will normally be present in the assay medium, as well as stabilizers for the assay medium and the assay components. Frequently, in addition to these additives, additional proteins may be included, such as albumins, or surfactants, particularly non-ionic surfactants, binding enhancers, e.g., polyalkylene glycols, or the like.

Inhomogeneity—a state of a member of a specific binding pair that manifests itself by the non-uniform migration of the sbp member in a separation process, such as electroseparation. The inhomogeneity may arise in an sbp member because of heterogeneity resulting from the presence of a plurality of molecules of the sbp member that have slight differences. An example of such a situation is a polyclonal antibody that has specificity for a certain antigen. The polyclonal antibody is a mixture of various antibody molecules that, although such molecules have similar specificity for a cognate (that molecule for which the antibody exhibits specificity) antigen, they are different because they recognize different sites on the cognate antigen. This condition can give rise to a spectrum of mobilities for the polyclonal antibody, thereby resulting in a broad, poorly defined band during migration. Another example inhomogeneity is an sbp member conjugated to a label. The labeling of the sbp member results in a distribution of molecules of the labeled sbp member where the molecules differ in number of labels attached or the position of attachment of the labels. Other examples of inhomogeneity are variable sites and degrees of glycosylation of proteins, variable lengths of polynucleotides, variable degrees of aggregation of membrane bound receptors, etc.

Masking inhomogeneity—process by which the effect of inhomogeneity of an sbp member on the mobility of such sbp member is significantly reduced or eliminated thereby resulting in a sharp, well-defined band of the sbp member during migration in a separation process such as electroseparation.

Electroseparation—separation of components in a liquid by application of an electric field, preferably, by electrophoresis (electrokinetic flow) or electroosmotic flow. Various forms of electroseparation include, by way of example and not limitation, free zone electrophoresis, gel electrophoresis, isoelectric focusing and isotachophoresis.

Capillary electroseparation—electroseparation, preferably by electrokinetic flow, including electrophoretic, dielectrophoretic and/or electroosmotic flow, conducted in a tube or channel of about 1–200 micrometer, usually, about 10–100 micrometers cross-sectional dimensions. Usually, the capillary is a channel in a wafer or film comprised of silver, glass or plastic. In one embodiment an apparatus for carrying out a capillary electroseparation comprises an electroseparation channel containing an electrically-conductive medium, an injection zone, a mixture comprising sample and specific binding members and a source of voltage.

Become localized—in the context of the present invention particles migrate uniformly to become localized during electroseparation when label that becomes attached to such particles in an assay can be readily differentiated from label that remains free. Usually, this requires that the particles become localized in a sharp, well-defined band. The width of the band depends on the size of the capillary, the nature of the migration medium, interactions of the particles with the capillary walls, ionic strength, viscosity of the medium magnetic fields, and the like. Again, the idea of the present invention is to achieve sufficient localization such that a separation of bound and free species can be achieved.

Conjugate—a molecule comprised of two or more molecules bound together, optionally through a linking group, to form a single structure. The binding can be made either by a direct connection (e.g., a chemical bond) between the molecules or by use of a covalently attached linking group (covalent attachment) or by non-covalent specific binding to a complementary sbp member (non-covalent attachment).

Synthetic particles—non-naturally occurring particles of at least about 20 nm and not more that about 20 microns, usually at least about 100 nm and less than about 2 microns, preferably from about 100 nm to about 500 nm in diameter. The particle may be organic or inorganic, swellable or non-swellable, porous or non-porous, having any density, but preferably suspendable in water. The particles may be composed of a material that can be transparent, partially transparent, or opaque. The particles may or may not have a charge. It is a feature of the present invention that inhomogeneity of sbp members may be masked using non-charged systems instead of the highly charged systems known in the art. However, the particles may be charged but not in the sense that the charge is the primary factor in the separation of the free and bound species.

The particles may be solid or synthetic vesicles or oil droplets and may be latex particles or other particles comprised of organic or inorganic polymers; lipid bilayers; silicon particles; metal sols; dendrimers, and so forth and may be diamagnetic or paramagnetic.

The organic particles are normally polymers, either addition or condensation polymers, which are readily dispersible in a medium used for electroseparation. The organic particles are adsorptive or functionalizable as to bind at their surface, whether directly or indirectly, an sbp member.

The particles can be synthesized directly or derived from naturally occurring materials that have been synthetically modified. Synthetic assemblies such as lipid bilayers, e.g., liposomes and non-phospholipid vesicles, are one form of synthetic particle useful in the present invention. Among organic polymers of particular interest are polysaccharides, particularly cross-linked polysaccharides, such as agarose, which is available as Sepharose, dextran, available as Sephadex and Sephacryl, cellulose, starch and the like addition polymers such as polystyrene, polyacrylamide, homopolymers and copolymers of derivatives of acrylate and methacrylate, particularly esters and amides having free hydroxyl functionalities. Metal sols include gold, selenium and other metals.

The particles are usually polyfunctional or are capable of being polyfunctionalized or are capable of being bound to an sbp member through specific or non-specific covalent or non-covalent interactions. A wide variety of functional groups are available or can be incorporated. Exemplary functional groups include carboxylic acids, aldehydes, amino groups, cyano groups, ethylene groups, hydroxyl groups, mercapto groups and the like. When covalent attachment of an sbp member to the particle is employed, the manner of linking is well known and is amply illustrated in the literature. See, for example, Cautrecasas, *J. Biol. Chem.* (1970) 245:3059. The length of any linking group may vary widely, depending upon the nature of the compound being linked, the nature of the particle, the effect of the distance between the compound being linked and the particle on the binding of sbp members to their cognates and the like.

For the most part, one or more of a non-oxocarbonyl group are employed including nitrogen and sulfur analogs, a phosphate group, an amino group, alkylating agent such as halo or tosylalkyl, oxy (hydroxyl or the sulfur analog, mercapto) oxocarbonyl (e.g., aldehyde or ketone), or active olefin such as a vinyl sulfone or $\alpha,\beta$-unsaturated ester. These functionalities are then linked to amine groups, carboxyl groups, active olefins, alkylating agents, e.g., bromoacetyl, to form the linking member. Where an amine and carboxylic acid or its nitrogen derivative or phosphoric acid are linked, amides, amidines and phosphoramides will be formed. Where mercaptan and activated olefin are linked, thioethers will be formed. Where a mercaptan and an alkylating agent are linked, thioethers will be formed. Where aldehyde and an amine are linked under reducing conditions, an alkylamine will be formed. Where a carboxylic acid or phosphate acid and an alcohol are linked, esters will be formed. Common functionalities in forming a covalent bond between the linking group and the molecule to be conjugated are alkylamine, amidine, thioamide, dithiol, ether, urea, thiourea, guanidine, azo, thioether and carboxylate, sulfonate, and phosphate esters, amides and thioesters.

The ratio of sbp member to particle in the sbp member-synthetic particle conjugate may vary greatly from as little as one sbp member per particle to particles that have surfaces that are fully coated with sbp members. Preferably, the particle surfaces are at least about 5% saturated with sbp members, more preferably, at least about 25% saturated with sbp members.

It may be desirable in the present invention to treat particles to which an sbp member has been attached with an agent to block non-specific binding sites, for the second member of the pair, and the like. For this purpose the particles may be treated with a non-specific protein material such as bovine serum albumin (BSA), bovine gamma globulin (BGG), non-fat dry milk, gelatin, protein or peptide hydrolysates, and so forth. The concentration of such material is about 0.01 to 1% by weight.

Synthetic particles of uniform dimension—in one embodiment of the present invention the synthetic particles are selected to have uniform dimension, i.e., all of the individual particle molecules should have substantially the same dimension. In the broadest sense the degree of uniform dimension is determined functionally as that resulting in optimizing the masking of the inhomogeneity of the sbp member to which the synthetic particles are attached. Consequently, the degree of uniform dimension is such that, in an electroseparation process, the mobility of the sbp member to which the particles are attached is substantially the same such that the sbp member migrates in a sharp, well-defined band. The dimensions of the synthetic particles of uniform dimension should be within about 20%, preferably, about 15%, more preferably, about 5%, of each other. Often, a compromise is made between the dimensions of the particles for effective examination and that which produces narrow bands on electrophoresis.

Synthetic particles of uniform dimension may be obtained in the process for preparing the synthetic particles, which are well known techniques. For example, such particles may be prepared by emulsion polymerization (polymers), sonication, (sols and vesicles) and pressure filtration through filters with defined pore size (vesicles).

Paramagnetic or diamagnetic particles—synthetic particles usually with relatively low magnetic susceptibility of at least about $1 \times 10^{-5}$ emu/Oecm3, preferably, about $10^{-2}$ to $8 \times 10^{-3}$ emu/g. Exemplary of the magnetic component of the paramagnetic particle that renders the particle magnetic but not able to magnetize other materials are intrinsically paramagnetic materials such as iron, cobalt, nickel, lanthanides, and the like, either in the free metal form or in the form of a complex, salt, oxide or the like. In one embodiment, the paramagnetic particles have a core of the paramagnetic component, optionally, a polymeric shell, and a surface comprising functional groups such as hydroxyl, silicate, carboxyl, amino, phosphate and the like for linking to an sbp member. The surface of the paramagnetic particle may be coated with proteins such as albumin, non-specific immunoglobulin, avidin, fetuin, and so forth, or a carbohydrate such as chitosan, dextran and the like, or combinations thereof. Alternatively, the paramagnetic component can be incorporated into a synthetic particle such as, for example, impregnating the paramagnetic substance in a polymeric matrix. See, for example, Whitesides, et al., *Advances in Biotechnology* (1983) 1(5):144–148. Coating the paramagnetic particles with macromolecules can increase colloidal stability. This can be done by direct adsorption of high molecular weight polymers or by functionalizing the surface of the particles and then binding macromolecules to the functional groups. Emulsion polymerization and grafting techniques provide a means for coating magnetic particles with polymers.

The paramagnetic particles should be readily suspendable and form stable, preferably colloidal, suspensions and should separate in a few seconds in a capillary subjected to a magnetic field strength of 1 to 5 Kgauss. Exemplary of particles useful in the present invention are nanosize particles from Milteny Biotec, Inc. (MACS Microbeads), and larger size beads (about 1 micron) from Japan Synthetic Rubber (JSR), Dynal (Lake Success, N.Y.) and Bangs Laboratories.

Magnetic field—the strength of the magnetic field applied to the migration medium is sufficient to permit the migration of the sbp member-paramagnetic particle conjugate in a sharp, well-defined band to allow separation of free and bound species. The strength of the magnetic field is usually about 0.1 to 10 Kgauss, preferably, about 1 to 5 Kgauss. The magnetic field is applied to the medium in the electroseparation device, which is usually a capillary. Accordingly, the electroseparation device is disposed adjacent the magnetic field source and the magnetic field is applied during the electroseparation step to inhibit flow of the complex at a predetermined location along the capillary.

Oil droplets—fluid particles comprised of a lipophilic compound coated and stabilized with an emulsifier that is comprised of amphiphilic molecules such as, for example, phospholipids, sphingomyelin, albumin and the like. The phospholipids are based upon aliphatic carboxylic acid esters of aliphatic polyols, where at least one hydroxylic group is substituted with a carboxylic acid ester of from about 8 to 36, more usually of from about 10 to 20 carbon atoms, which may have from 0 to 3, more usually from 0 to 1 site of ethylenic unsaturation and at least 1, normally only 1, hydroxyl group substituted with phosphate to form a phosphate ester. The phosphate group may be further substituted with small aliphatic compounds which are of two or higher functionality, generally having hydroxyl or amino groups.

The oil droplets can be made in accordance with conventional procedures by combining the appropriate lipophilic compounds with a surfactant, anionic, cationic or nonionic, where the surfactant is present in from about 0.1 to 5, more usually from about 0.1 to 2 weight percent of the mixture and subjecting the mixture in an aqueous medium to agitation, such as sonication or vortexing. Illustrative lipophilic compounds include hydrocarbon oils, halocarbons including fluorocarbons, alkyl phthalates, trialkyl phosphates, triglycerides, etc.

An sbp member will usually be adsorbed to the surface of the oil droplet or bonded directly or indirectly to a surface component of the oil droplet. The sbp member may be incorporated into the liquid particles either during or after the preparation of the liquid particles. The sbp member will normally be present in from about 0.5 to 100, more usually 1 to 90, frequently from about 5 to 80 and preferably from about 50 to 100 mole percent of the molecules present on the surface of the particle.

The following is a list, by way of illustration and not limitation, of amphiphilic compounds, which may be utilized for stabilizing oil droplets: phosphatidyl ethanolamine, phosphatidyl choline, phosphatidyl serine, dimyristoylphosphatidyl choline, egg phosphatidyl choline, diapalmitoylphosphatidyl choline, phosphatidic acid, cardiolipin, lecithin, galactocerebroside, sphingomyelin, dicetylphosphate, phosphatidyl inositol, 2-trihexadecylammoniumethylamine, 1,3-bis(octadecyl phosphate)-propanol, stearoyloxyethylene phosphate, phospholipids, dialkylphosphates, sodium dodecyl sulfate, cationic detergents, anionic detergents, proteins such as albumin, non-ionic detergents, etc.

Other compounds may also be used which have lipophilic groups and which have been described previously. For the most part, these compounds will be alkylbenzenes, having alkyl groups of from 6 to 20 carbon atoms, usually mixtures of alkyl groups, which may be straight or branched chain, and having a carboxyl group, an hydroxylic group, a polyoxy alkylene group (alkylene of from 2 to 3 carbon atoms), carboxylic group, sulfonic acid group, or amino group. Aliphatic fatty acids may be used which will normally be of from about 10 to 36, more usually of from about 12 to 20 carbon atoms. Also, fatty alcohols having the carbon limits indicated for the fatty acids, fatty amines of similar carbon limitations and various steroids may also find use.

The oil droplets can comprise a fluorocarbon oil or a silicone oil (silicon particle). Such droplets are described by Giaever in U.S. Pat. Nos. 4,634,681 and 4,619,904 (the disclosures of which are incorporated herein in their entirety). These droplets are formed by dispersing a fluorocarbon oil or silicone oil in an aqueous phase. The droplets are prepared by placing a small amount of the selected oil (generally, such oils are commercially available) in a container with a larger amount of the aqueous phase. The liquid system is subjected to agitation to bring about emulsification and then centrifuged. The homogeneous phase is removed and the residual droplets are resuspended in an aqueous buffered medium. The above centrifugation and decantation steps can be repeated one or more times before the droplets are utilized.

Sbp members can be bound to the droplets in a number of ways. As described by Giaever, the particular sbp member, particularly a proteinaceous sbp member, can be coated on the droplets by introducing an excess of the sbp member into the aqueous medium prior to or after the emulsification step. Washing steps are desirable to remove excess sbp member. Functionalization of the oil introduces functionalities described above for linking to sbp members and labels. Other oil droplets described by Giaever also find use in the present invention.

Vesicles—microvesicles of approximately spherical shape, having a diameter that is at least about 25 nm and not more than about one micron, usually, less than about 400 microns. Preferably, the diameter of the vesicles is less than about two microns so as to limit settling or floatation.

The outer shell of a vesicles consists of an amphiphilic bilayer that encloses a volume of water or an aqueous solution. Vesicles with more than one bilayer are referred to as multilamellar vesicles. Vesicles with only one bilayer are called unilamellar vesicles. Vesicles in which the amphiphilic bilayer is comprised of phospholipids are referred to as liposomes. Phospholipids employed in preparing liposomes utilizable in the present invention can be any phospholipid or phospholipid mixture found in natural membranes including lecithin, or synthetic glyceryl phosphate diesters of saturated or unsaturated 12-carbon or 24-carbon linear fatty acids wherein the phosphate can be present as a monoester, or as an ester of a polar alcohol such as ethanolamine, choline, inositol, serine, glycerol and the like. Particularly preferred phospholipids include L-a-palmitoyl oleoylphosphatidylcholine (POPC), palmitoyl oleoylphosphatidylglycerol (POPG), L-a-dioleoylphosphatidylglycerol, L-a(dioleoyl)-phosphatidyl ethanolamine (DOPE) and L-a(dioleoyl)-phosphatidyl D-(4-(N-maleimidomethyl) cyclohexane-1-carboxyamido) ethanol (DOPE-MCC).

The phospholipids in the bilayer may be supplemented with cholesterol and may be replaced with other amphiphilic compounds that have a polar head group, usually charged, and a hydrophobic portion usually comprised of two linear hydrocarbon chains. Examples of such substituents include dialkylphosphate, dialkoxypropylphosphates wherein the alkyl groups have linear chains of 12–20 carbon atoms, N-(2,3-di(9-(Z) octadecenyloxy))-prop-1-yl-N,N,N-trimethyl-ammonium chloride (DOTMA), as disclosed in U.S. patent application Ser. No. 811,146 filed on Dec. 19, 1985, which is hereby incorporated herein by reference, sphingomyelin, cardiolipin, and the like.

For use in the present invention the liposomes should be capable of binding to an sbp member. The liposomes utilized in the present invention will usually have sbp members bound to the outer surface of the lipid vesicle.

Liposomes may be produced by a variety of methods including hydration and mechanical dispersion of dried phospholipid or phospholipid substitute in an aqueous solution. Liposomes prepared in this manner have a variety of dimensions, compositions and behaviors. One method of reducing the heterogeneity and inconsistency of behavior of mechanically dispersed liposomes is by sonication. Such a method decreases the average liposome size. Alternatively, extrusion is usable as a final step during the production of the liposomes. U.S. Pat. No. 4,529,561 discloses a method of extruding liposomes under pressure through a uniform pore-size membrane to improve size uniformity.

Labeling of droplets and liposomes will often involve, for example, inclusion of thiol or maleimide or biotin groups on the molecules comprising the lipid bilayer. An sbp member may then be bound to the surface by reaction of the particles with one of these materials that is bound to a sulfhydryl reactive reagent, a sulfhydryl group, or avidin, respectively. Sulfhydryl reactive groups include alkylating reagents such as bromoacetamide and maleimide.

Sbp members can be attracted to the surface of the vesicles by weak hydrophobic interactions, however such interactions are not generally sufficient to withstand the shear force encountered in an electroseparation method. It is preferable to covalently bond sbp members to a vesicle that has been functionalized, for example by use of DOPE-MCC, as shown above, by combining the vesicle with the selected sbp member functionalized with a mercaptan group. For example, if the sbp member is an antibody, it may be reacted with S-acetylmercaptosuccinic anhydride (SAMSA) and hydrolyzed to provide a sulfhydryl-modified antibody.

Latex particles—signifies a particulate water suspendable water insoluble polymeric material usually having particle dimensions of 20 nm to 20 $\mu$m, more preferably 100 to 1000 nm in diameter. The latex is frequently a substituted polyethylene such as: polystyrene-butadiene, polyacrylamide polystyrene, polystyrene with amino groups, poly-acrylic acid, polymethacrylic acid, acrylonitrile-butadiene, styrene copolymers, polyvinyl acetate-acrylate, polyvinyl pyridine, vinyl-chloride acrylate copolymers, and the like. Non-crosslinked polymers of styrene and carboxylated styrene or styrene functionalized with other active groups such as amino, hydroxyl, halo and the like are preferred. Frequently, copolymers of substituted styrenes with dienes such as butadiene will be used.

An sbp member may be physically adsorbed on the surface of the latex particle or may be covalently bonded to the particle. In cases wherein the sbp member is only weakly bound to the surface of the latex particle, the binding may in certain cases be unable to endure particle-to-particle shear forces encountered during an electroseparation method. Therefore, it may be preferable to covalently bond sbp members to the latex particles under conditions that will minimize adsorption. This may be accomplished by chemically activating the surface of the latex. For example, the N-hydroxysuccinimide ester of surface carboxyl groups can be formed and the activated particles to reduce nonspecific binding of assay components to the particle surface, are then contacted with a linker having amino groups that will react with the ester groups or directly with an sbp member that has an amino group. The linker will usually be selected to reduce nonspecific binding of assay components to the particle surface and will preferably provide suitable functionality for both attachment to the latex particle and attachment of the sbp member. Suitable materials include maleimidated aminodextran (MAD), polylysine, aminosaccharides, and the like. MAD can be prepared as described by Hubert, et al., Proc. Nat'l. Acad. Sci. (1978) 75(7):3143.

In one method, MAD is first attached to carboxyl-containing latex particles using a water-soluble carbodiimide, for example, 1-(3-dimethylaminopropyl) 3-ethyl carbodiimide. The coated particles are then equilibrated in reagents to prevent nonspecific binding. Such reagents include proteins such as bovine gamma globulin (BGG), and detergent, such as Tween 20, TRITON X-100 and the like. A sbp member having a sulfhydryl group, or suitably modified to introduce a sulfhydryl group, is then added to a suspension of the particles, whereupon a covalent bond is formed between the sbp member and the MAD on the particles. Any excess unreacted sbp member can then be removed by washing.

Metal sols—particles comprised of a heavy metal, i.e., a metal of atomic number greater than 20 such as a Group IB metal, e.g., gold or silver. Metal sol particles are described, for example, by Leuvering in U.S. Pat. No. 4,313,739, the disclosure of which is incorporated herein by reference in its entirety. Such sols include colloidal aqueous dispersion of a metal, metal compound, or polymer nuclei coated with a metal or metal compound.

The metal sols may be of metals or metal compounds, such as metal oxides, metal hydroxides and metal salts or of polymer nuclei coated with metals or metal compounds. Examples of such metals are platinum, gold, silver mercury, lead, palladium, and copper, and of such metal compounds are silver iodide, silver bromide, copper hydrous oxide, iron oxide, iron hydroxide or hydrous oxide, aluminum hydroxide or hydrous oxide, chromium hydroxide or hydrous oxide, vanadium oxide, arsenic sulfide, manganese hydroxide, lead sulfide, mercury sulfide, barium sulfate and titanium dioxide. In general, the metals or metal compounds useful may be readily demonstrated by means of known techniques. It is sometimes advantageous to use sots comprised of dispersed particles consisting of polymer nuclei coated with the above mentioned metals or metal compounds. These particles have similar properties as the dispersed phase of pure metals or metal compounds, but size, density and metal contact can be optimally combined.

The metal sol particles may be prepared in a large number of ways, which are in themselves known. For example, for the preparation of a gold sol, Leuvering refers to an article by G. Frens in *Nature Physical Science* (1973) 20:241. The metal sol particles can be modified to contain various functional groups as described above for linking to an sbp member. For example, polymeric bonding agents can be used to coat the particles such as polymers containing thiol groups that bond strongly to many heavy metals or silylating agents that can bond and form polymeric coatings as, for example, by reaction of metal particles with trialkoxy aminoalkylsilanes as described in EPO Patent Appl. 84400952.2 by Advanced Magnetics for coating magnetic particles.

Hydrodynamic flow properties—movement of particles relative to a fluid, usually an aqueous liquid. Usually, the particles are immersed in the fluid.

Modify hydrodynamic flow properties—a change in the hydrodynamic flow properties. In the context of the present invention particles are employed to change the hydrodynamic flow properties of a specific binding pair member in an electroseparation.

Sieving gel—sieving gels are commercially available gels with defined pore sizes for separating different size solutes. Examples of suitable sieving gel components are, by way of illustration and not limitation, agarose, ficoll, polysucrose, polyacrylamides and synthetic amphiphilic gel forming compounds.

Silica particles—silica particles are commercially available. Examples thereof by way of illustration and not limitation are Percoll® (Pharmacia Biotech) and the like.

Dendrimers—highly defined tree-like branched polymers having discrete molecular weights. See, for example, D. A. Tomalia, *Angew. Chem.* (1990) 102:119–157 for a review. Also see *Advanced Materials* (Weinheim, Ger.) (1994) 6:529–539 for the construction of larger molecules using dendrimer building blocks instead of atoms.

Covalent binding—direct attachment of two molecules by means of a chemical bond directly linking the two molecules or by means of a linking group chemically bound to and bridging the two molecules.

Non-covalent binding—attachment of two molecules by means of specific binding interactions.

Assay—a method for determining a substance capable of binding to a specific binding pair member, for example, for determining an analyte or detecting the degree of binding of a compound to a receptor. The determination may be qualitative or quantitative. Such assays depend on specific binding of a ligand to its receptor and include receptor binding assays, immunoassays, ligand/binding assays, polynucleotide assays, particularly polynucleotide hybridization assays, and cell surface binding assays. The assays may be utilized for drug discovery and screening, studies of receptors, detection of drugs and other substances, DNA detection, DNA sequencing, genetic analysis, monitoring of gene expression, and so forth. One particular assay is the immunoassay, which is a specific binding assay in which the reagents include an antibody.

Heterogeneous assay—an assay wherein free labeled species is separated from a labeled species that is bound to another species such as an sbp member. The separation may be carried out by physical separation, e.g., by transferring one of the species to another reaction vessel, and so forth, and may include one or more washing steps. The separation may be nonphysical in that no transfer of one or both of the species is conducted, but the species are separated from one another in situ such as by differences in size, differences in mobility, differences in charge to mass ratio and the like. Nonphysical separation techniques are more applicable to the area of microfluidics. In addition, magnetic beads may be employed for capture and separation. In the heterogeneous assay the activity of a label is not affected by the reaction of specific binding pair members with one another. Regardless of the means of separation, the signal from the label may be measured from one or both of the separated species.

Homogeneous assay—an assay wherein free labeled species is not separated from a labeled species that is bound to another species such as an sbp member. The signal from the label is significantly different between the free labeled species and that which is bound and, thus, can be measured without separation.

Immunoassay—a specific binding assay in which the reagents include an antibody.

Complex—a moiety formed by the binding of two or more sbp members to one another. The complex is usually bimolecular in the sense that it comprises a molecule of a first sbp member and a molecule of a second sbp member, which is the cognate sbp member, i.e., the sbp member recognized by the first sbp member. However, the complex may be termolecular or higher molecularity.

Electroactive substance—a substance that undergoes a change in charge as a result of electrochemical oxidation or reduction. Generally, an overall weak charge is replaced by either an overall positive or negative charge or vice versa or the charge is reversed from positive to negative or vice versa. For example, diketones such as oxidized ascorbic acid and quinones are neutral and form readily ionizable enediols and hydroquinones, respectively, that become negatively charged. Alpha-diketones are subjected to electrochemical reduction when in proximity of an anode in contact with the assay medium.

Alternatively, neutral stable cations are formed, for example, from benzidenes by electrochemical oxidation.

Negatively charged N,N-dialkyl amino phenolate ions are oxidized to cationic quinone imines or the process can be reversed to provide negatively charged N,N-dialkylaminophenolates. These redox reactions are usually conducted at an electrode other than the electrode that drives the electroseparation. Various electron transfer agents can be added to the medium to facilitate the redox reactions such as, for example, ferrocenes, aliphatic amines, heavy metal salts, iodide, etc. Normally, many molecules of the electroactive substance are bound to an sbp member so that, upon oxidation or reduction, there will be a profound change in charge that, preferably, will lead to aggregation and localization of the sbp member. This can usually be achieved most readily by oxidation of anionic electroactive substances with formation of neutral or positive products.

Electrochemical oxidation or reduction—the process by which an electroactive substance undergoes oxidation or reduction electrochemically. As mentioned above, in general, the conditions chosen for the electrochemical oxidation or reduction involve contacting the medium with an electrode at the desired location along the capillary.

As mentioned above, in a broad aspect the present invention concerns methods for masking inhomogeneity of a member of a specific binding pair (sbp) employed in a capillary electroseparation. To achieve this end synthetic particles are bound to the sbp member prior to capillary electroseparation. In one embodiment the synthetic particles are characterized in that they migrate uniformly during capillary electroseparation. The particles may be bound to the sbp member either covalently or non-covalently. A particle-sbp member conjugate may be prepared and used as a reagent in the electroseparation. Alternatively, the particles may become bound to the sbp member in situ by virtue of the sbp member having a binding member and the particle having a complementary binding member. For example, the sbp member may be attached to biotin and the synthetic particle may be attached to avidin. Other binding partner pairs that may be used, by way of example and not limitation, are fluorescein-antibody for fluorescein, N-dinitrophenyl lysine-antibody for dinitrophenyl, two complementary oligonucleotides, single stranded DNA-single stranded DNA binding protein, and so forth.

The nature of the synthetic particles employed determines the manner in which the particles are treated during the electroseparation to achieve separation from free labeled sbp members. Synthetic particles that have uniform dimensions and charge, generally can be caused to migrate uniformly during capillary electroseparation although protein carriers, excipients, surfactants and salts may be required to prevent peak broadening due to non-specific binding to the walls of the capillary.

Paramagnetic particles need not have uniform dimensions but preferably should be small enough to remain suspended for minutes or hours. Localization is achieved by application of a magnetic field during the capillary electroseparation. This is usually accomplished by orienting a magnetic field at a site along the capillary where the particles are to be concentrated. Label associated with the particles can then be detected at this site or the filed can be removed and the electroseparation continued so that the particles move to another site along the capillary where the label is detected.

In another embodiment particles that modify the hydrodynamic flow properties of the sbp member are used. Such particles include, by way of illustration and not limitation, polymeric particles such as latex particles, lipid vesicles such as liposomes, metal sols, silica particles, dendrimers, oil droplets and the like. In this embodiment the particles are subjected to a filter or a viscous medium such as a sieving gel during the capillary electroseparation. The viscous medium may be present throughout the capillary so as to slow the migration of the particles relative to labeled sbp members. Alternatively, a portion of the capillary can be cooled to cause gelation at a specific site and cause the particles to accumulate at that site. Another approach is to introduce the gel or a mechanical filter at a site in the capillary where the particles are to accumulate.

As mentioned above, one embodiment of the present invention is a method for conducting a capillary electroseparation specific binding assay for an analyte. The method involves the electroseparation of a labeled first member of a specific binding pair that is bound in a complex from labeled first member that is not bound in the complex. The complex comprises the first member and a second member of a specific binding pair. A combination is provided comprising a sample suspected of containing an analyte, a labeled first member of a specific binding pair, and a second member of a specific binding pair under conditions for forming a complex between labeled first member and the second member. The second member either initially or subsequent to the formation of the complex is covalently or noncovalently bound to synthetic particles that migrate uniformly during electroseparation.

The combination is usually provided in a suitable medium, usually, an electrically conductive medium. Any suitable electrically conductive medium are buffered medium containing can be used. Electrical conductivity is imparted by the presence of dissolved salts, usually, at concentrations greater than about 10 mM, preferably, greater than about 50 mM. The medium may also contain other components depending on the nature of the synthetic particles used in the present invention. For example, for particles that modify the hydrodynamic flow properties of the sbp member, a sieving gel is employed. Examples of other components that may be included in the medium are agarose, polyacrylamide, silica, gelatin, Smartgel® and other commercially available gel agents.

The pH of the medium is usually about 4 to 10, preferably, about 5 to 9, more preferably, 6 to 8. It is to be understood that the size of the particles utilized in the present invention may be subject to pH considerations. The determination of particle size and pH may be accomplished empirically by one skilled in the art by carrying out electrophoresis experiments and examining the effect of pH and particle size on the band width of a particle band formed during electrophoresis. The temperature employed during the electroseparation is usually about 15 to 50° C., more usually about 15 to 50° C. The ionic strength and viscosity of the medium are optimized for a particular application where a sieving gel is not used. In general, the higher the ionic strength of the medium, the worse the separation between the particle species. The ionic strength of the medium is usually about 0.005 to 0.6 mM, more typically, about 0.02 to 0.10 mM. The length of the separation path is also a consideration. In general, the longer the length of separation path, the worse the separation. The separation path is usually about 1 mm to 20 cm, more typically, about 2 mm to 5 cm. The length of the separation path varies depending on the particular species. Thus, for example, for single base DNA separation a typical separation length is about 4 cm.

The combination is subjected to electroseparation by introducing each of the components of the combination into an electroseparation channel of an electroseparation device that may be part of a capillary electroseparation assay device. A capillary electroseparation assay device comprises an electroseparation channel with two electrodes positioned to be in electrical contact with fluid within a capillary wherein the capillary has at least one entry port and one exit port and a provision for detection of a label. The capillary is generally about 5 mm to 2 m, preferably, 1 cm to 10 cm in length. Although glass or plastic capillary tubes can be used in this invention, preferably, the capillary will be an embossed, molded, etched, machined or otherwise imbedded channel on a first surface which is covered by a membrane, film or rigid solid having a second surface that conforms to the first surface but for the presence of the channel and any openings necessary for electrical contacts and introduction and removal of fluids. The resulting device may be rigid or flexible and preferably at least a portion of the capillary well will be transparent.

An electric potential is then applied to the electrically conductive medium contained with the channel to effectuate migration of the components within the combination. Generally, the electric potential applied is sufficient to achieve electroseparation of the free and the bound labeled species. The electric potential required to impart electrophoretic motion is typically applied at two or more sites along the capillary or a channel a high voltage source operated at electric field strengths generally ranging from several hundred volts per centimeter to several thousand volts per centimeter. The application of the electric potential can be controlled either via manual operation, a waveform generator or computer control. It is in the purview of the present invention to vary the strength of the electric potential during the electroseparation and assay. For example, an initial stage at higher electric potential may be followed by application of a lower electric potential during the period of time for complex formation. Then, the electric potential may be increased to complete the electroseparation. One skilled in the art will be capable of determining the suitable electric potentials for a given set of sbp members, particles and electroseparation medium.

All of the above parameters for the electroseparation including those for the medium and the electric potential are usually optimized to achieve maximum separation of free and bound species. This may be achieved empirically and is well within the purview of the skilled artisan.

Following the electroseparation a determination is made as to whether the complex is formed. Such a determination can be achieved by employing a signal producing system as mentioned above in conjunction with a detector. Detection of the signal and the nature of the detector depend upon the nature of the signal producing system utilized. If the reporter molecule is an enzyme, additional members of the signal producing system would include enzyme substrates and so forth. The product of the enzyme reaction is preferably a luminescent product, usually a fluorescent dye, which can be detected spectrophotometrically, or a product that can be detected by other spectrometric or electrometric means. If the label is a fluorescent molecule, the medium can be irradiated and the fluorescence determined. Where the label is a radioactive group, a scintillator will be included in the capillary well or in the medium and the radioactive emission detected photometrically. Likewise, where the label is a chemiluminescent substance, photometric detection can be used.

In another embodiment of the present invention, the second member either initially or subsequent to the formation of the complex is bound to a binder for the second member wherein the binder causes the complex to become localized during electroseparation. The combination is subjected to electroseparation and a determination is made as to whether the complex is formed. As the binder for the second sbp member, one may employ antibodies directed specifically to the second sbp member. For example, where the second sbp member is an antibody that has a difference from the first sbp member such as a different light chain, anti-k or anti-l chain antibodies are utilized that bind specifically to the second sbp member by virtue of binding to the different light chain. Alternatively, the second sbp member is an antibody that is raised in a particular species different from the first sbp member and an antibody directed against the species is used. For example, where the second sbp member is an antibody that is raised in rabbits and the first sbp member is a murine monoclonal antibody, an anti-rabbit IgG may be used that is raised in a suitable host such as a goat. Alternatively, the second sbp member can be conjugated to a ligand and the binder may be a receptor for the ligand. Examples of such ligands and receptors are biotin-avidin, N-dinitrophenyl lysine-antibody for dinitrophenyl, two complementary oligonucleotides, single stranded DNA-single stranded DNA binding protein, and the like. The amount of the binder is generally sufficient to bind all of the second sbp member. Generally, it is preferable for the binder to be attached to a particular polymer that facilitates separation. However, in some cases the binder itself may suffice for this purpose. This will occur when the binder is highly charged relative to the second sbp member. Thus, for example, when the second sbp member is conjugated to a DNA binding protein, the binder will be DNA, which carries a very high negative charge.

Following the binding of the binder to the complex, the combination is subjected to electroseparation. It may be desirable in certain circumstances to employ a sieving gel in the electroseparation medium to assist in providing localization of the complex bound to the binder and achieve appropriate separation of the free and bound species, i.e., the complex from the uncomplexed first and second sbp members. Subsequently, a determination is made as to whether the complex is formed. The method of detection of complex formation is generally the same as that described above.

One specific embodiment of an assay in accordance with the present invention, by way of example and not limitation, is a membrane-receptor competitive binding assay.

In this example, cell membrane receptors are attached to solid-phase capture media for facilitating the use of protein receptors in a microfluidic-based assay. Solid-phase attachment of the receptor is achieved in one of several ways, including, e.g., the use of activated paramagnetic beads or other synthetic particles.

In the assay cellular membranes are harvested from tissues or cell cultures expressing the receptor of interest. The typical crude homogenate contains particles of widely varying sizes. These membranes, by virtue of the protein, carbohydrate, and lipid moieties on their surface, are capable of binding to particles. For example, plastic beads, polymer beads such as latex beads, paramagnetic beads, and the like may be used. These beads may be activated by attachment to additional molecules to enhance the immobilization of the desired target molecule(s). This latter principle is exemplified by lectins, which can be covalently attached to a latex particle and which extend the affinity of the new particle for receptors and membranes by binding to the carbohydrate chains existing on these macromolecules.

The receptor-beads can be more uniformly dispensed based on their size, shape, and/or density. The process of transfer and/or capture is facilitated further by conferring a magnetic property to the beads.

In this particular assay embodiment, activated paramagnetic beads of relatively uniform size are coupled to membrane receptors to deliver a predetermined quantity of target receptor to a vessel for reaction with various potential agonists and/or antagonists. The beads may be magnetic beads commercially available from Dynal (Dynabeads®). The Dynabeads are superparamagnetic, monodispersed polystyrene microspheres coated with antibodies or other binding moieties that selectively bind to the target molecule, including cells, genes, bacteria, or other biomolecules. This assay is particularly applicable for receptors belonging to the seven transmembrane family or similar proteins wherein the sequence of amino acids traverse the membrane multiple times. These targets, e.g., the G-protein coupled receptor (or GPCR), are more likely than others to require the physical environment of the membrane lipid bilayer for physiologically relevant interactions. The dopamine receptor is a specific example in the broader class of GPCR proteins.

A typical membrane-receptor competitive-binding assay in regard to the above is described next. The non-isotopic assay comprises two binding events. The primary receptor-ligand affinity reaction can be written generally as:

$$\frac{L_i + L^* + (R)}{\text{"free" in supernatant}} = \frac{(R) - L^* + (R) - L_i}{\text{"bound" in solid-capture phase}}$$

where the library test compound $L_i$ and labeled ligand $L^*$ compete for receptor binding sites (R) on the immobilized cell membrane protein. Once the unbound ligand $L^*$, which remains "free" in the supernatant, is removed, then the bound ligand, which is complexed with the immobilized receptor beads, can be detected using a fluorophore-labeled secondary binding protein. If a biotinylated ligand is employed in the primary bioaffinity reaction, then solid-phase fluorescence detection is possible based on the following binding reaction:

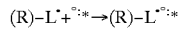

where $^\circ:*$ represents, for example, an avidin-fluoroscein conjugate, as the other member of the secondary specific binding pair.

Other protocols based on methods of the invention are also possible. For example, a detection scheme may be employed based upon depletion monitoring of the labeled ligand $L^*$. Protocols for this embodiment of the invention are described below.

A microfluidic assay device 100, configured generally as illustrated in FIG. 1, is employed in the assay. The components of microfluidic assay device 100 as illustrated in FIG. 1 are as follows: inlet reservoir 102 for buffer solution; inlet reservoir 104 for library test compound ligand i ($L_i$); inlet reservoir 106 for biotin-labeled ligand conjugate, biotinylated tracer; inlet reservoir 108 for fluorophore-labeled secondary binding protein, or fluorescent tracer; inlet reservoir 110 for bead-immobilized, membrane-bound receptor; inlet reservoir 112 for wash buffer solution; inlet reservoir 114 for solution used to cleave the fluorophore-tag from the fluorescent tracer conjugate; inlet reservoir 116 for capture compound; outlet reservoir 124 for waste solution from binding assay from the fluorescent tracer conjugate; outlet reservoir 126 for waste capture compound; outlet reservoir 128 for waste supernatant from binding; incubation, separation and detection chamber 125; secondary capture and detection chamber 135.

Before outlining the assay protocol that is conducted on device 100 ("on-board"), reagent preparation conducted first ("on-line") includes the following:

1) Magnetic latex beads, preactivated to covalently bind protein, are first bound to a lectin such as wheat germ agglutinin (WGA). Upon completion of this step, unreacted or exposed bead surface is blocked from nonspecific interactions by incubation with a saturating concentration of carrier protein such as bovine serum albumin or gelatin.

2) The WGA coated beads are next coincubated with coil membranes having on them the receptor of interest. This interaction may also conclude with another blocking step, to remove or inactivate potential sites of nonspecific binding.

The bioanalytical assay proceeds on microfluidic device 100 as follows:

1) A fixed quantity of receptor-beads are introduced into a reservoir 110, which is part of microfluidic device 100. The receptor-beads are transferred, by means of an applied magnetic field, to a "reaction chamber" 125 in fluid communication with reservoir 110. In this particular assay protocol, the beads are held in this reaction chamber for the duration of the procedure.

2) Next, the compound $L_i$ to be tested for binding ability is added by electrokinetic means to chamber 125 from reservoir 104, prior to, or simultaneously with, the addition of a standard compound $L^*$ of known binding properties. This latter compound contains a member of a signal producing system, for example, covalently attached biotin.

3) After an appropriate series of electrokinetically driven wash steps using wash buffer from reservoir 112, a determination is made for the amount of unknown compound $L_i$ that binds by determining the degree to which It displaces the standard compound $L^*$. This is measured by introducing the secondary fluoro-labeled binding protein into reaction chamber 125 from reservoir 108 and allowing the complex of compound and receptor, (R)–$L^*$, to react with the streptavidin which binds biotin with high affinity. The amount of streptavidin captured is monitored directly for a fluorescent label, e.g., fluorescein, associated with the streptavidin.

4) In one form of this assay, the fluorescent label may be attached via a disulfide bond denoted by ":". This bond Is readily cleaved under reducing conditions. Therefore, dithiothreitol, or beta-mercaptoethanol stored in reservoir 114 may be used to release the fluorescent label, denoted by "*".

5) The fluorescent labeled species can then be separated from other reactants by electrokinetic or hydrodynamic enhanced electroseparation techniques. To facilitate detection, the magnetic beads may be immobilized at a site along the capillary path 125 by application of a magnetic field. The fluorescent label may be detected at that site or at a site 135 downstream therefrom. The fluorescent label may be detected in the fluorescent labeled species or the fluorescent label may be cleaved and detected separately.

A wide variety of applications of the present invention involving, for example, cell biology, molecular biology, HLA tissue typing, and microbiology are therefore possible. More specifically, for example, the invention may be applied to methods for DNA purification from whole blood and other samples, to mRNA isolation, to solid phase cDNA synthesis, to cell isolation, and so forth.

Bioanalytical binding assays based on affinity reactions and multi-phase separation and/or localization methods are provided as examples of embodiments of the current invention. The tracer-binder separation step can include electrophoretic and/or biomagnetic processes. Experimental protocols are described that utilize synthetic particles to which an sbp member is attached. Advantages of this approach are numerous including the masking of binding site heterogeneity, more uniform flow distributions, format flexibility, and so forth. The use of hydrophilic low-binding surfaces, when combined with capture beads provides for a powerful method to minimize non-specific binding and to control the size of the resulting vesicles in the preparation of the crude receptor. In addition, the flexibility in assay design as afforded by microfluidic devices, when combined with solid-phase capture particles, is illustrated by way of a number of examples using various specific binding pairs and detection formats.

Figure 2:
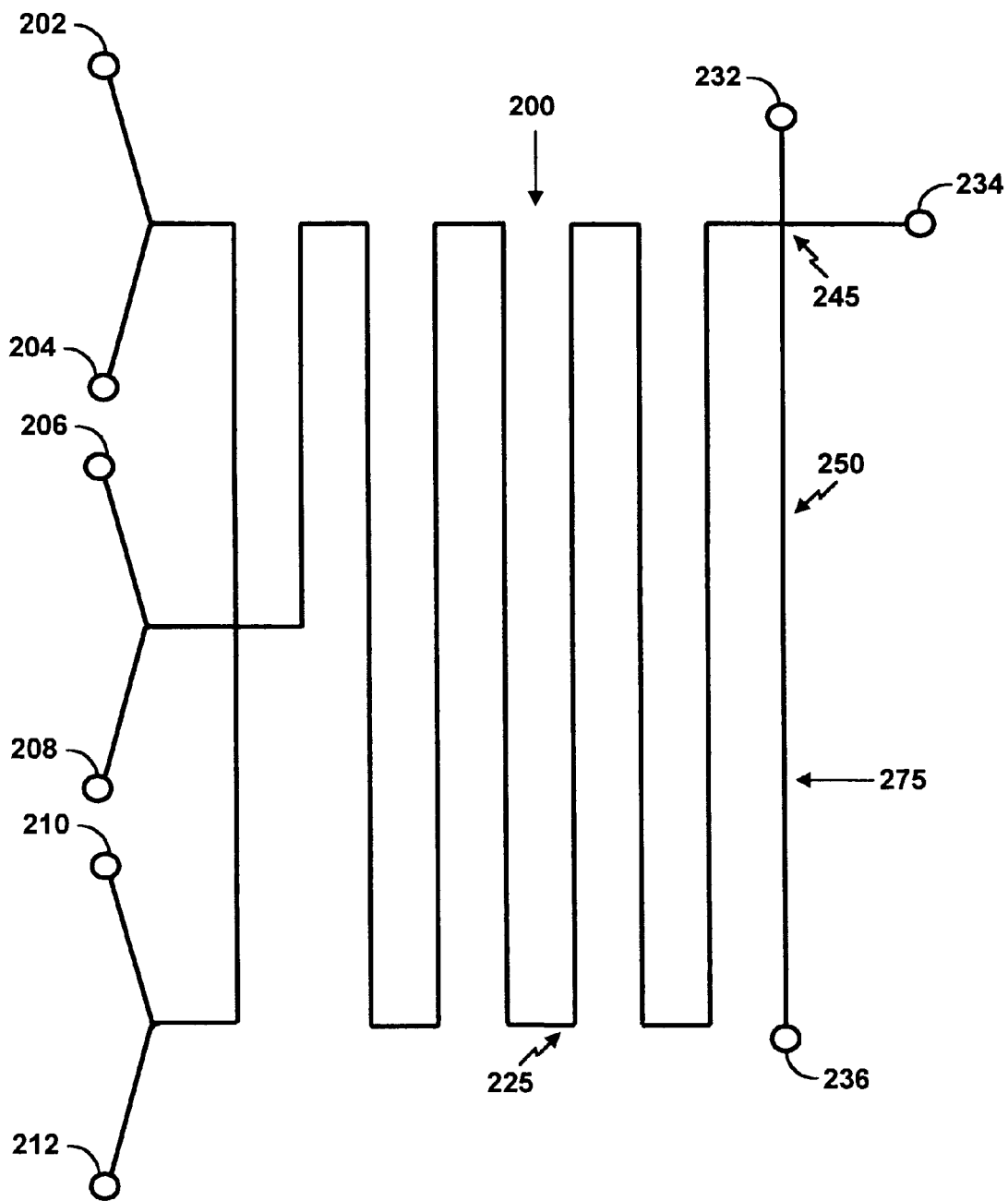
FIG. 2. is a diagram of one embodiment of a device in which a method for performing sandwich immunodiagnostic assays may be carried out in accordance with the present invention.

FIG. 2 provides an illustration of a microfluidic device 200 configuration and method for carrying out a highly sensitive sandwich immunoassay that is readily amenable to high throughput clinical diagnostic applications. The sandwich assay reaction can be written generally as follows:

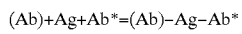

Reagents are introduced into an incubation channel 225 for mixing and affinity binding followed by injecting a plug of the reaction mixture for electrophoretic separation and then detection of the sandwich complex, (Ab)–Ag–Ab*.

Microfluidic device 200 may be utilized in performing sandwich immunodiagnostic assays. Device 200 comprises inlet reservoir 202 for antibody, Ab, specific to particular antigen wherein Ab is bound to plastic beads of relatively uniform size of about one micron; inlet reservoir 204 for (Ab) dilution buffer; inlet reservoir 206 for antigen, Ag; inlet reservoir 208 for Ag dilution buffer; inlet reservoir 210 for fluoro-labeled antibody, Ab*, specific to particular antigen; inlet reservoir 212 for Ab* dilution buffer; incubation channel 225; inlet reservoir 232 for running buffer; outlet reservoir 234 for waste products; outlet reservoir 236 for detection product waste; injection cross 245; outlet reservoir 250 for waste; detection chamber/zone and detector 275; and secondary capture and detection chamber 236.

An example of an immunodiagnostic competitive binding assay is based on the following affinity reaction:

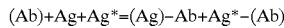

where the labeled Ag* and unlabeled Ag antigen of interest compete for the target antibody (Ab), which is attached to plastic beads of relatively uniform size. Because an assay protocol based upon this bioaffinity reaction is similar to the receptor-ligand competitive assay, it will not be further discussed here. The above protocol was used in the Example presented below.

Receptor-ligand competitive binding assays employing microfluidic-based multi-phase monitoring schemes are also exemplary of the assays to which the present invention has application. Utilization of cell surface receptors for the discovery and characterization of pharmacologically active compounds has become an important tool in the pharmaceutical industry. Of particular relevance is the capability to screen in an automated and highly parallel manner large numbers of library test compounds generated by combinatorial and other chemical means. Both primary and secondary screens are of significant general interest in addition to being related to the methods according to this invention. Other embodiments include solid-phase assays for the purpose of characterizing particular isolated cell-membrane receptors. Assay protocols include those wherein a ligand labeled with a fluorophore, enzyme or biotin binds competitively with unlabeled ligand for the active sites of the receptor yielding an analytical signal that can be related to the affinity of the drug, toxin, or other test compound of interest relative to the standard tracer. In addition, monitoring ligand-induced receptor-mediated cell response to external stimuli is useful for elucidating cell signal-transduction mechanisms.

In the above assays two distinct detection approaches arise when direct detection of both "bound" and "free" tracer is possible. Employing a microfluidic approach is particularly amenable to dual detection schemes. In one approach involving a capture assay for receptor-bound fluorophore-labeled ligand, detection can be accomplished by solid-phase monitoring of "bound" tracer or downstream detection of cleaved fluorophore tag (Ab capture & measure enhanced signal).

Instead of using commercially available (Sigma) particles or the methods provided above, alternative procedures for preparing solid-phase capture materials may be employed. More specifically, Concanavalin A-coated magnetic particles such as, e.g., JSR CIM-31 carboxy beads (0.8 micron in diameter), can be prepared in a three step process: 1) particles are first coated with bovine serum albumin (BSA); 2) succinic anhydride is then reacted with BSA coated particles; and 3) concanvalin A (ConA) is coated on the carboxy BSA particles. Once synthesized, the ConA-coated carboxy magnetic particles can be used to capture membrane-bound receptors while also minimizing the non-specific binding of receptor-selective fluorescent tracers. Depending on the particular assay protocol, this immobilization or capture step may be carried out prior to the binding assay or during the course of the assay.

Examples of competitive receptor-ligand binding assays are described above in which pre-conjugated receptor-beads are employed. In another embodiment of the invention, solid-phase capture particles are introduced during the course of the bioanalytical assay to separate free and bound species. In this particular embodiment, receptor, tracer and test compound are allowed to incubate statically or in a flow configuration. After a set time, coated particles are added to the reaction mixture, or the mixture is moved through a region of a microchannel in which beads are located. Having been synthesized for this purpose, the magnetic beads selectively capture the membrane-bound receptors. By applying a magnetic field, the beads are immobilized and the free fluorescent tracer in the supernatant is measured. In addition to this depletion assay, the bound fluorescent tracer can be measured in the solid phase or the captured fluorophore can be released using a detergent and then measured. More specifically, both formats have been demonstrated for a D2 GPCR assay employing a NAPS (from Molecular Probes)-tracer, which may be synthesized by known methods, D2 membrane receptors obtained from SF9 cells and ConA-coated JSR CIM-31 magnetic particles. A NAPS-biotin competitor was used as a representative test compound.

Selective bead modifications have other beneficial attributes. More specifically, in capillary and chip-based heterogeneous enzyme assay such as, e.g., kinase assays, the enzyme substrate such as, e.g., cdc2 peptide (see, for example, Johnson, et al., *J. Peptide Research* (1997) 50:365–371), has been shown to interact with the surface of particular beads, yielding inhomogeneities that are detrimental to assay performance. To mask these inhomogeneities, beads have been coated with ConA. In a similar synthesis protocol as above, carboxy particles are reacted with aminodextran, yielding diglycolic anhydride (DGA) beads having a diameter of 200 nm. By coating the DGA beads with ConA, the interaction between the kinase substrate CDC2 and the beads in minimized. For example, in bead manipulation experiments performed on-board microfluidic polymeric cards, the ConA-DGA beads yield sharp peaks in the resulting electropherogram (signal versus time), whereas the uncoated DBA beads yield peaks with ill-defined shoulders. In this embodiment of the invention, surface modified polymethylmethacrylate (PMMA) microchannels were employed to enhance electroosmotic transport of the solid phase caputre particles. A 50 nM HEPES pH 7.4 running buffer was used in these experiments.

Other examples of assays that may be carried out using the present invention are a nicotinic acetylcholine receptor assay using a fluorophore-labeled ligand and neuronal nicotinic acetylcholine receptor and ligand-gated ion channel. For the latter the assay procedure generally described above may be used to quantitatively characterize the interactions of cholinergic agents with the nicotinic acetylcholine receptor (nAChR), a molecular switch that contributes to intercellular communication within the central nervous system. When the two α-subunits of the cell-surface receptor bind with the neurotransmitter acetylcholine, or its analogs nicotine and carbamylcholine, a conformational change occurs in the five subunit supramolecular postsynaptic receptor protein that results in the formation of an open channel. The subsequent influx of positive charges ($Na^+$, $K^+$, and some $Ca^{2+}$) through the ion channel causes a depolarization of the cell transmembrane potential. Because neurostimulated excitation-contraction (EC) coupling plays an important role in synaptic transmission at the neuromuscular junction, nAChR assays are widely employed within the pharmaceutical industry for investigating lead compounds. More specifically, assays are used to characterize potential new drugs and assist in the understanding of their function. In addition, the nAChR can be used as a molecular recognition element in bioanalytical assays and sensors for detecting biological and chemical warfare agents.

The invention also has application to Scatchard analysis and dose response analysis.

A. Scatchard analysis: In addition to primary screening as described above, a microfluidic device similar to that of FIGS. 1 and 2 and multi-phase assay protocols utilizing the invention may be used for investigating further the isolated cell-membrane receptor. In one protocol a fixed concentration of ligand labeled with a fluorophore binds to the active binding sites of the receptor for a range of receptor concentrations.

A "zero-dose" saturation analysis enables the receptor/labeled-ligand binding interactions to be characterized, including identification of the proper range of binder and tracer concentrations where quantitative bioanalytical detection is possible. α-Bungarotoxin (α-Bgt), an important antagonist that binds to the acetylcholine site with a high affinity, is extensively utilized in the study of the nAChR, although it does not have any clinical use The concentration of the fluorescein-labeled a-bungarotoxin tracer, L*, is held constant as the concentration of the nicotinic acetylcholine receptor is varied. As receptor concentration is increased, the saturation behavior of the "bound" response, B*=T*–F*, can be obtained by directly measuring the fluoro-intensity of the bound ligand, B*, in the solid-capture phase and indirectly by measuring the fluoro-intensity of the background-corrected "total" tracer T* and the "free" tracer F* in the supernatant. The background signal arises from the intrinsic fluorescence of the low-density components of the biological matrix.

Saturation behavior lends itself to a Scatchard analysis. A plot of B*/F* (bound/free) versus free F* yields the dissociation constant K* for receptor/labeled-ligand binding and the maximum number of receptor binding sites $B_{max}$. Characterizing the zero-dose response as a function of a wide range of both tracer and receptor concentrations can be carried out to optimize assay performance.

B. Dose-response analysis: Using a microfluidic-assay card device similar to those depicted in FIGS. 1 and 2, dose-response behavior for a given ligand-receptor system is obtained by varying the concentration of the test compound for a fixed amount of labeled ligand (tracer) and receptor. The fluorescent-based receptor binding assay described above may be used for investigating cholinergic drugs, mostly muscle relaxants. Labeled ligand, i.e., α-bungarotoxin fluorescein isothiocyanate conjugate (α-Bgt-FITC), binds competitively with unlabeled library compound using a sequential saturation procedure. After a separation step, the free label concentration is determined via LIF according to one of several assay protocols described below.

Another assay of interest is a fluorescence-based receptor binding assay for investigating cholinergic ligands that interact with the α-binding site of the nAChR are presented. The assay system is based on sequential saturation of the cell-surface receptor by test compound $L_i$ and the fluorescein-labeled α-bungarotoxin (α-Bgt:FITC) tracer (see, e.g., Molecular Probes). The fluorescence-based receptor assay (FRA) may be used to obtain dose-response data for a number of cholinergic agents, including the agonist carbamylcholine and various antagonists (mostly muscle relaxants) including α-bungarotoxin, pancuronium, d-tubocurarine, gallamine, decamethonium, and hexamethonium. The $IC_{50}$'s of the ligands can be determined directly from the binding results employing fluoroscein-labeled bungarotoxin to compete for the α-binding sites of the nicotinic acetylcholine receptor using a sequential saturation procedure.

Another group of compounds binds to the same site on the receptor but blocks acetylcholine's physiological activity. Generally, such compounds can be classified as non-depolarizing drugs (antagonists) that include gallamine, d-tubocurarine, pancuronium, and hexamethonium. An important antagonist,.

Another assay is a benzadiphine receptor competitive binding dual assay employing a biotinylated ligand and secondary SBP. A fluorometric receptor-based dual assay protocol may be used. The robust competitive-binding assay is particularly amenable to high-throughput pharmaceutical drug screening because "off-the-shelf" reagents are employed instead of having to synthesize special fluorophore-labeled ligand conjugates. The trade-off for universal reagents however, is a more complex dual assay protocol.

In this embodiment of a dual assay, the first of two binding reactions is a primary receptor-ligand competitive binding reaction employing a biotinylated-ligand.

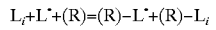

$$L_i + L^* + (R) = (R) - L^* + (R) - L_i$$

In the primary binding event, a library test compound $L_i$ competes with the biotin-labeled drug $L^*$ for the active binding sites of the bead-immobilized membrane receptor (R). After separation of the "free" from the "bound" $L^*$ conjugate, the biotinylated drug in the supernatant from the first incubation step may be monitored. Various detection schemes are possible, including solid-phase detection of (R–$L^*$) and/or depletion monitoring of the labeled ligand $L^*$. Protocols for each will be briefly outlined where a robust secondary binding assay is employed.

The premise for the secondary assay is that the "free" biotinylated ligands $L^*$ and the biotin beads compete for a limited number of biotin binding sites on the high-affinity avidin binding protein according to the following bioaffinity reaction:

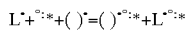

where ( )* denotes biotin labeled beads, e.g., biotin-conjugated paramagnetic or polystyrene particles. The avidin-fluorophore (A:F) conjugate is denoted by °:* in the secondary binding reaction above, where * represents the fluorescent tag. After incubation, washing leaves only the fluorophore-labeled avidin captured onto the biotin solid phase.

In addition to the "bound" detection-based assay, described above, "free" ligands in the supernatant can be electrokinetically moved downstream for detection by means of a secondary "on-board" assay protocol. In contrast to the more direct detection scheme and exemplified in the nAChR assay above, the concentration of free ligand in the suspension above the immobilized membrane receptor can be determined by a solid-phase assay utilizing a secondary binding pair, e.g., avidin-biotin or streptavidin-biotin.

Benzodiazepine (BzdR) drugs act on the central nervous system to produce hypnotic, muscle relaxing, tranquilizing and anticonvulsant activities and are widely prescribed in clinical practice. Highly sensitive assay methods to determine their concentration in tablets, blood, urine, etc. are required to evaluate their pharmacological effects and to investigate the interactions of potential new drugs with the receptor.

In this example, (R) in the reaction above represents the benzadiphine receptor-immobilized paramagnetic beads or (BzdR), and L* represents a biotin-1012-S drug conjugate, which has been reported in the literature. $L_i$ can represent one of many benzadiphine drugs or drug analogs, including clonazepam and lorazepam. In this embodiment of the invention, a benzadiphine receptor assay is described for the purpose of illustration only. Other receptor systems, including soluble receptors such as the interleukins, or cell surface receptors as part of whole cells, are also amenable to microfluidic-based assays similar to that presented here.

A Scatchard analysis may be carried out to measure the bound tracer response obtained from the saturation data. A Scatchard plot resulting from the saturation data is obtained by varying the tracer concentration for a fixed protein binder concentration.

A fluorometric receptor-based dual assay (FRDA) for the benzodiazepines clonazepam (O) and lorazepam (I) employing a biotinylated-drug probe and biotin-immobilized microfluidic card can yield dose-response for the system. The competition reaction between the biotin-1012S conjugate and a benzodiazepine drug give a well-defined dose-response curve.

Another assay is a whole cell receptor assay device and method for secondary screening and functional analyses. Receptor-ligand competitive binding assays are a useful preliminary means for screening a large number of compounds for their therapeutic potential. However, improved high throughput bioanalytical techniques are needed for characterizing the functional properties of receptor-mediated signaling and other cell transduction mechanisms. One embodiment of an assay provides for simultaneously monitoring the response of a plurality of living cells to a wide variety of external stimuli. Because cell-based assays can be designed to be particularly sensitive to changes in the membrane potential or ion concentration fluctuations, (e.g., intracellular calcium) or pH, the microfluidic devices and solid-phase assay methods in accordance with the present invention may be used to analyze novel receptor targets, determine receptor activation/inactivation, biological/functional response, develop agonist/antagonist profiles, and study structure-activity relationships. This nondestructive detection method is compatible with cell culture and growth along with being applicable to a wide variety of cells, including adherent and non-adherent cells, eukaryotes and prokaryotes. More specifically, cell types include mammalian, (e.g., fibroblasts, epithelial and endothelial cells, lymphocytes, neurons, macrophages, muscle cells), insect, bacterial, yeast, fungi, microbial cells, and viruses and/or hosts. In addition, this microfluidic approach is applicable to high throughput analysis of cell effector agents including neurotransmitters and ion channel modulators (e.g., CNS-cholinergic, adrenergic, dopaminergic drugs, CNS-excitatory amino acids, glutamate, kainic acid, and the like), antiviral and antineoplastic agents, hormones, prostaglandins, growth factors, cytokines, MHC complexes, enzyme activators/inhibitors, and potentially toxic substances. Thus, these non-invasive, real-time, physiological measurements provide the investigator with an enormous amount of information in a short time about metabolic activity, signal transduction pathways, and receptor-mediated mechanisms. As in other embodiments of assays previously discussed, receptors whose activation can be detected using whole-cell assays routinely arise in the fields of pharmacology, neurobiology, cardiology, immunology, microbiology, and oncology, among others. More specifically, signal transduction groups detected include G protein coupled receptors (e.g., adrenergic, bradykinin, chemokines, cholecystokinin, dopaminergics, endothelin, muscarinics, nociceptin, opioid, prostaglandin, and serotonin), ligand-gated ion channels (e.g., excitatory amino acids and neuronal nAChR), tyrosine kinase (e.g., insulin-like IGF, epidermal EGF, nerve NGF, fibroblast FGF growth factors), T-cell receptors and the interleukins.

Another assay is a homogeneous enzyme receptor assay. Another embodiment of a solid-phase assay to which the present invention may be applied is an enzyme-amplified receptor assay (ERA). In this assay, the enzyme activity of a drug conjugate is modulated upon binding with the immobilized membrane receptor. A receptor-ligand competitive binding reaction can be generally represented by the following bioaffinity reaction:

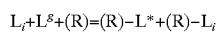

where (R) represents membrane receptors attached to solid-phase particles, which can be immobilized by, for example, magnetic or electromagnetic means. The homogeneous assay does not require a separation step. Enzyme activity has been engineered such that its enzyme activity becomes inhibited upon binding with the receptor.

As with the bead-based assays described above, the ERA method may be employed to investigate a wide variety of pharmacologically important receptors for their binding properties, including receptor activity and dose-response behavior. A specific example is provided here for illustration purposes only.

In this example, a nicotinic acetylcholine receptor assay employing an enzyme-labeled ligand or fluorophore as the tracer is put forth as an example of a representative ERA system. An assay procedure for quantifying the binding of the hallucinogen phencyclidine (PCP), antipsychotic agents including tricyclic antidepressants (TCA's) and toxins all to the channel-site of the nicotinic acetylcholine receptor (nAChR) was reported using an enzyme-labeled drug as the tracer. However, the drug screen has proven to be irreproducible due to its sensitivity to the experimental conditions of the assay, e.g., the heterogeneity associated with the distribution of the receptor. In contrast to the original work, the bead-based multi-assay format described herein provides for a bioanalytical screening method that is readily amenable to high throughput automation. In addition, masking heterogeneities should increase analytical detection limits.

In principle, homogeneous assays are faster and easier to perform than heterogeneous assays because no bound/free separation step is necessary. However, due to matrix effects, it is typically difficult to measure a very low concentration in a complicated sample by homogeneous assay. In practice, a heterogeneous assay has a detection limit 100-fold lower than the most sensitive homogeneous assay. Nonetheless, in certain non-diagnostic applications, including pharmaceutical drug discovery, homogeneous assays offer sensitivity limits that are more than adequate for high-throughput primary screening. Thus, homogeneous assays hold much promise for their use in conjunction with microfluidic-based devices and methods.

The present invention also has application to polynucleotide assays such as DNA assays and to other studies of polynucleotides such as hybridization studies and the like. For this purpose a highly-flexible, miniature, automated device capable of performing a broad range of DNA-based assays may be used. The multi-functional instrument provides for collecting DNA from a raw sample, amplifying the DNA using the polymerase chain reaction (PCR), and analyzing the DNA product by Taqman assays, fragment sizing, and ihybridization. Thus, on-chip fractionation of DNA from other cellular components may be conducted. In addition, the reusability of a capillary electrochromatography (CEC) microchannel for determining PCR product lengths can be achieved. A hybridization technique using surface-activated magnetic beads which can be reused for multiple assays may be conducted. All of these DNA sample preparation and analysis features may be conducted in a single reusable laminated plastic microfluidic platform, using electroosmotic pumping of fluids, external optical detection, and magnetic capture and release of magnetic beads.

Following the PCR reaction, a variety of procedures can be performed on the device. To facilitate optical detection, amplified product must first be contacted with a fluorophore. Product can then be introduced into a variety of hybridization (H) zones, which can be individually charged with specifically functionalized beads from another bead bank. After hybridizing on the beads, optical fluorescence detection may be used to identify the presence of pathogens of interest. DNA fragment sizing and identification can be performed in the CEC channel prior to, or in place of the hybridizations. To increase the rate of analysis and detection, product can be dumped to waste at any time if the absence of pathogens is confirmed.

A microprocessor control unit activate the system of electroosmotic pumps to provide valveless motion of packets of fluid through the interconnecting flow channels. Valves at critical locations are configured using pneumatically driven elastomers against specially microfabricated features in the plastic surface. These are activated as required by the control system. Sensors are read by the microprocessor and the information analyzed to determine the results of the assay. The system is readily amenable to later addition of telemetry devices to enable external control and transmission of results.

DNA analysis is the most specific of current pathogenic testing methods, including flow cytometry, capillary electrophoresis, dielectrophoresis and mass spectrometry. Deadly airborne bacteria such as *Bacillus globigii* (Bg) can be detected by their specific sequence. DNA also can be amplified using PCR or other techniques to increase the signal from the pathogen, an essential feature for biological warfare detection systems in which extremely low concentrations of pathogens must be detected quickly. Concentration of aerosol samples is a critical issue since deadly concentrations can be as much as six orders of magnitude lower than detectable limits.

Following the lysing of spores/cells, DNA is extracted so that extraneous proteins and other biological matter does not interfere with the amplification and separation methods of the DNA. To accomplish this, micro-scaled bead-based methodologies upstream of the amplification and detection processes. For cases in which it is desired to screen all types of DNA in the sample, cells can be contacted with lysate to release all intracellular fluid upstream of the bead bed. The released DNA can then be collected non-specifically onto silica particles in the bed for subsequent elution to the PCR chamber. When the analysis is intended only for a particular cell type, magnetic beads functionalized to bind to specific cell types can fractionate the desired cells out of the sample stream. The subsequent transport of lysate through the bead bed will release the desired DNA for downstream amplification.

In the above approach, magnetic beads for the hybridization assays will be electroosmotically injected into the flow stream and trapped in incubation chambers using small permanent magnets mounted in close proximity to the flow path. Additional optical analysis can be made at that time or the beads can be introduced to some other assay such as off-chip flow cytometry. The expended beads can be released by moving the permanent magnet a short distance away from the bead chamber, and flushed to waste; new beads can be charged into the hybridization zone for additional assays. Several sample aliquots can be sent in parallel to different zones to test simultaneously for a number of different pathogens. This entire process will be microprocessor controlled.

The present invention also comprises kits for conducting a capillary electroseparation specific binding assay. The kit comprises in packaged combination a labeled member of a specific binding pair that is capable of binding to suspendable particles in the assay, the suspendable particles, and a capillary electroseparation assay device. Another embodiment in accordance with the present invention for conducting a capillary electroseparation specific binding assay are kits comprising in packaged combination a labeled first member of a specific binding pair, a second member of a specific binding pair bound to, or capable of binding to, an electroactive substance, and a capillary assay device. The reagents for the kits may be packaged in the same or separate containers, so that the concentration of the reagents provides for substantial optimization of the method and assay. The reagents may each be in separate containers or various reagents can be combined in one or more containers depending on the cross-reactivity and stability of the reagents. Under appropriate circumstances one or more of the reagents in the kit can be provided as a dry powder, usually lyophilized, including excipients, which on dissolution will provide for a reagent solution having the appropriate concentration for performing a method or assay in accordance with the present invention. The kit can also include additional reagents depending on the nature of the method for which the kit is used. For example, the kit may include a binder for the second sbp member where the method involves binding a binder to the complex to provide for more uniform mobility. Another example of an additional reagent is a sieving gel where the method includes the use of such a gel. The kit can further include other separately packaged material, ancillary reagents such as buffers, and so forth.

EXAMPLE

The invention is demonstrated further by the following illustrative example. Parts and percentages are by weight unless otherwise indicated. Temperatures are in degrees Centigrade ° C. unless otherwise specified. The following preparations and examples illustrate the invention but are not intended to limit its scope.

Particle-based Sandwich Assay
1. Selection of Particles as Solid Matrix.

For the purposes of the present example, two features were desired, namely, that the particle have relatively little to no heterogeneity in size and give no fluorescence signal when laser induced fluorescence (LIF) detection is applied. The particles employed were polystyrene latex particles from Interfacial Dynamics, Portland, Oreg. Five different sizes of particles were first tested on capillary electrophoresis (CE) using a device from Beckman Instruments P/ACE 5000 to check their heterogeneity and fluorescence. Both UV absorbance and fluorescence detection were used The results were summarized in Table I. The sizes of these particles range from 0.041 to 0.40 $\mu$m. They all gave UV absorbance and no fluorescence. Separation conditions: capillary 27 cm long 50 $\mu$m inside diameter (id) fused silica capillary; 7 cm effective separation distance. Separation buffer: 1 mM 2-[(2-amino-2-oxoethyl)amino]ethanesulfonic acid (ACES) buffer (pH 5.98). Injection: 3s at 8 kV. Separation voltage; 12 kV, 1.1 $\mu$A, positive polarity. Detection UV absorbance at 254 nm.

During CE all the particles were well separated from neutral marker (mesityl oxide) when the effective separation distance was 7 cm. The half-height peak width for 0.321 $\mu$m particle was much wider than those of other particles. The electropherogram of 0.0671 $\mu$m particles showed a small step before real peak arises. This may suggest some slight amount of heterogeneity of these two particles.

The fluorescence of these particles was also tested using LIF detection. Separation conditions: capillary 47 cm long, 50 $\mu$m id fused silica capillary; 7 cm effective separation distance. Separation buffer: I mM ACES buffer (pH 5.98). Injection: 3s at 8 kV. Separation voltage; 20 kV, 1.1 $\mu$A, positive polarity. LIF detection. (A) buffer; (B) 0.041 $\mu$m; C) 0.067 $\mu$m (D) 0.11 $\mu$m; (E) 0.321 $\mu$m; (F)0.40 $\mu$m. No detectable fluorescence was observed for all the particles tested, even at very high particle concentration. Therefore, polystyrene latex particles with the diameters of 0.041, 0.11 and 0.40 $\mu$m were selected as potential candidates as capture antibody (unlabeled) carrier to form a sandwich complex with antigen and secondary antibody (fluorophore labeled).
2. Particle Coating with Monoclonal Antibody.

Anti-insulin monoclonal antibody (Cortex Biochem, San Leandro, Calif.) was employed as the capture antibody, which was physically adsorbed on the particle surface. Phosphate buffered saline (PBS) containing 100 mM phosphate, 150 mM NaCl at pH 7.2 was chosen as incubation buffer for antibody coating. Particles 0.11 $\mu$m (1/120 dilution) were incubated with monoclonal antibody (Mab) in 0.23×PBS and 0.46×PBS at pH 7.2, respectively. The buffer's ionic strength was gradually increased to the level required (i.e., particles were suspended in 0.05×, 0.1×, 0.25×, 0.5× and 1×PBS consecutively). The amount of Mab used was calculated based on the equations from Bangslab, Champaign, Ill., for monolayer coverage. For 100 $\mu$L particle solution, 5.46 $\mu$L Mab was added. The particle suspension was occasionally vortexed at room temperature for 1 hour. After overnight rotating at 4° C., particle pellets were formed on the eppendorf tube wall. Therefore, centrifugation was used to wash antibody coated particles.

Mab-coated particles were analyzed by CE. Comparison of (A) Mab coated particles; (B) uncoated particles. Separation conditions: capillary 27 cm long, 50 $\mu$m id using silica capillary; 20 cm active separation distance. Separation buffer: 5 mM phosphate buffer (pH 7.2). Injection: 1s at 2 kV for (A), 1s at 3 kV for (B). Separation voltage; 12 kV, 9 $\mu$A, positive polarity. Detection UV absorbance at 214 nm. The migration time of coated beads was shorter than uncoated beads. A new peak emerged when free Mab was added to the coated particles.
3. Assay between Mab Coated Particles and Insulin.

When insulin, Mab and insulin+Mab were tested on CE, all of them migrated out at about the same time. In order to clarify the complex formation process, FITC-insulin (from Sigma Chemical Company) was used as a tracer. Electropherograms were recorded for (1) Mab coated particles, FITC-insulin, and both of them and (2) uncoated particles mixed with FITC-insulin. Different electropherograms were obtained. This experiment demonstrates that the particles have been coated with Mab and Mab-coated particles have binding ability to insulin.

The assay between Mab coated particles and FITC-insulin gave a binding curve, namely, the plot of peak height of complex between Mab-coated particles and FITC-insulin vs. concentration of FITC-insulin. The peak height of complex increased as concentration of FITC-insulin increased. The plot showed a narrow linear binding region before it reached a plateau as expected.

Another experiment was also carried out by adding various amounts of Mab coated particles to a fixed amount of FITC-insulin solution. As the amount of Mab coated particles increased, amount of complex formation increased. A similar assay between free Mab and FITC-insulin was also performed.
4. Separation of Insulin Complexes.

A series of experiments were carried out to improve the separation between the two complexes, i.e., insulin-Mab and insulin-Mab-coated particles. The separation of these two complexes provides a direct indication of the separability of the sandwich complex Mab-particles-insulin-FITC-Mab') from free labeled antibody under the same conditions. The effects of the buffer's ionic strength, separation distance and applied voltage were Investigated. In this investigation the higher the ionic strength, the worse the separation and the longer the separation distance, the better the separation. The experimental results demonstrated that these two complexes were separable.
5. FITC Labeling of Secondary Monoclonal Antibody (Mab').

Fluorescein isothiocyanate (FITC) was used to label a secondary antibody (namely, monoclonal anti-insulin from Cortex Biochem) for sandwich complex formation and detection. The procedure followed was that suggested by the manufacturer. The antibody was diluted to 1 mg/ml and reacted with a large excess of FITC (molar ratio at 60), and hydroxylamine was used to stop the reaction. The labeled Mab' was purified through spin column to remove excess FITC. The final labeled Mab' was stored in 10 mM PBS containing 2 mM $NaN_3$. FITC-Mab' was tested on CE. The electropherograms showed one major peak with a little shoulder. The size of the shoulder changed during duplicate runs, and no trend was observed. Ultracentrifugation tube with 5,000 MW cutoff was used to remove any lower molecular weight material from FITC-Mab' solution. After centrifugation, the electropherogram was similar to that obtained before centrifugation. The shoulder of FITC-Mab' peak was still present, which more than likely was related to the antibody itself.

In order to improve FITC-Mab' peak shape, 0.02% BSA was added in running buffer. No improvement was achieved until higher concentration of 5 mg/mL of BSA or non-fat dry milk was present in sample buffer, which gave improvement in peak shape of FITC-mab' and in reproducibility.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A method for detecting the presence of an analyte in a sample employing capillary electroseparation in a microfluidic device where the binding of specific binding pair members results in an inhomogeneous complex, said method comprising:

combining in an assay mixture particles of uniform dimension to which one member of said specific binding pair is bound, said sample suspected of containing said analyte and a labeled compound which binds to said bound member of said specific binding pair or to said analyte;

subjecting said assay mixture to capillary electroseparation to provide a sharp band of particles; and detecting labeled member bound to said particles, as indicative of the presence of said analyte.

2. A method according to claim 1, wherein said particles are paramagnetic.

3. A method according to claim 1, wherein said particles are polymeric.

4. A method according to claim 1, wherein one of said members of said specific binding pair is a receptor.

5. A method according to claim 1, wherein said bound member is antisera.

6. A method according to claim 1, wherein said bound member is covalently bound.

7. A method for conducting a capillary electroseparation specific binding assay for a protein analyte using a microfluidic device, said method involving the electroseparation of a labeled first member of a specific binding pair, where the other member is said analyte, and said analyte becomes bound to a second specific binding pair member, that binds to analyte in the presence of binding of said analyte to said first member, said method comprising:

(a) incubating an assay mixture comprising a sample suspected of containing said analyte, said first member bound to particles of uniform dimension, and said second member in any order of addition, to form a complex, when said analyte is present, of said first member bound to said particles, said analyte, and said second member;

(b) electroseparating said assay mixture; and (c) determining whether said complex is formed.

8. A method according to claim 7, wherein at least one of said first and second members is antisera.

9. A method according to claim 7, wherein said particles are paramagnetic.

10. A method according to claim 7, wherein said particles are polymeric.

* * * * *